US009732153B2

(12) United States Patent
Carmon et al.

(10) Patent No.: US 9,732,153 B2
(45) Date of Patent: Aug. 15, 2017

(54) ANTIBODIES DIRECTED AGAINST SIGNAL PEPTIDES, METHODS AND USES THEREOF

(75) Inventors: Lior Carmon, Tel Aviv (IL); Riva Kovjazin, Ashkelon (IL)

(73) Assignee: VAXIL BIOTHERAPEUTICS LTD., Nes-Ziona (IL)

( * ) Notice: Subject to any disclaimer, the term of this patent is extended or adjusted under 35 U.S.C. 154(b) by 129 days.

(21) Appl. No.: 14/344,837

(22) PCT Filed: Sep. 13, 2012

(86) PCT No.: PCT/IL2012/050365
§ 371 (c)(1),
(2), (4) Date: Mar. 13, 2014

(87) PCT Pub. No.: WO2013/038412
PCT Pub. Date: Mar. 21, 2013

(65) Prior Publication Data
US 2014/0220028 A1 Aug. 7, 2014

Related U.S. Application Data

(60) Provisional application No. 61/535,017, filed on Sep. 15, 2011.

(51) Int. Cl.
| C07K 16/28 | (2006.01) |
| C07K 16/06 | (2006.01) |
| G01N 33/566 | (2006.01) |
| A61K 38/00 | (2006.01) |
| G01N 33/569 | (2006.01) |
| G01N 33/574 | (2006.01) |

(52) U.S. Cl.
CPC ......... *C07K 16/28* (2013.01); *G01N 33/5695* (2013.01); *G01N 33/56966* (2013.01); *G01N 33/57492* (2013.01); *G01N 2333/4725* (2013.01)

(58) Field of Classification Search
None
See application file for complete search history.

(56) References Cited

U.S. PATENT DOCUMENTS

| 4,816,567 A | 3/1989 | Cabilly et al. | |
| 2005/0244904 A1* | 11/2005 | Ng | G01N 33/558 435/7.92 |
| 2007/0196369 A1* | 8/2007 | Hoogenboom | 424/144.1 |
| 2009/0239246 A1* | 9/2009 | Pemberton | C07K 14/58 435/7.21 |
| 2011/0296545 A1* | 12/2011 | Srikumaran | C07K 14/70553 800/15 |

FOREIGN PATENT DOCUMENTS

| WO | 00/34787 A1 | 6/2000 |
| WO | 2005/019269 A2 | 3/2005 |
| WO | 2008/035350 A1 | 3/2008 |

OTHER PUBLICATIONS

Tang et al., (Clinical and Vaccine Immunology, 2010, 17:1903-1908).*
O'Connor et al. (Prostate Cancer and Prostatic Disease, 2005, 8:36-44).*
Levitin et al. (Journal of Biological Chemistry, 2005, 280:33374-33386).*
Berglund et al. (Protein Science, 17:606-613).*
Lyko et al., "Signal Sequence Processing in Rough Microsomes", The Journal of Biological Chemistry, vol. 270, No. 34, pp. 19873-19878, (1995).
Kovjazin et al., "Signal Peptides and Trans-membrane Regions are Broadly Immunogenic and have High CD8+ T Cell Epitope Densities: Implications for Vaccine Development", Mol Immunol., vol. 48, No. 8, pp. 1009-1018, (2011).
Martoglio, "Intramembrane proteolysis and post-targeting functions of signal peptides", Biochemical Society Transactions, vol. 31, Part 6, pp. 1243-1247, (2003).
Graham et al., "The polymorphic epithelial mucin: potential as an immunogen for a cancer vaccine", Cancer Immunol Immunother, vol. 42, pp. 71-80, (1996).
Ho et al., "Heterogeneity of Mucin Gene Expression in Normal and Neoplastic Tissues", Cancer Res, vol. 53, pp. 641-651, (1993).
Lacunza et al., "MUC1 oncogene amplification correlates with protein overexpression in invasive breast carcinoma cells", Cancer Genetics and Cytogenetics, vol. 201, pp. 102-110, (2010).
Treon et al., "Elevated soluble MUC1 levels and decreased anti-MUC1 antibody levels in patients with multiple myeloma", Blood, vol. 96, pp. 3147-3153, (2000).
Croce et al., "Tissue and serum MUC1 mucin detection in breast cancer patients", Breast Cancer Research and Treatment, vol. 81, pp. 195-207, (2003).
Gion et al., Comparison of the Diagnostic Accuracy of CA27.29 and CA15.3 in Primary Breast Cancer, Clinical Chemistry, vol. 45, No. 5, pp. 630-637, (1999).
Lu et al., Humoral Immunity Directed against Tumor-Associated Antigens As Potential Biomarkers for the Early Diagnosis of Cancer, Journal of Proteome Research, vol. 7, pp. 1388-1394, (2008).
Tang et al., "Strategies used for MUC1 immunotherapy: human clinical studies", Expert Rev. Vaccines, vol. 7, No. 7, pp. 963-975, (2008).

(Continued)

*Primary Examiner* — Julie Wu
(74) *Attorney, Agent, or Firm* — Susanne M. Hopkins; Roberts Mlotkowski Safran Cole & Calderon, P.C.

(57) ABSTRACT

Provided are methods employing antibodies directed against the signal peptide (SP) domain of various disease-associated polypeptides. These anti-SP antibodies detect cell surface expression of these SP domains and are used in methods of diagnosis and/or therapy. Provided is a method for determining the suitability for treatment of a subject suffering from a disease, whereby detection of cell surface expression of a specific SP indicates that the subject would benefit from therapy directed against this SP. Further, provided are methods for diagnosis of diseases based on the detection of endogenously produced anti-SP antibodies.

3 Claims, 16 Drawing Sheets

(56) References Cited

OTHER PUBLICATIONS

Kohler et al., "Continuous cultures of fused cells secreting antibody of predefined specificity", Nature, vol. 256, pp. 495-497, (1975).
Goding, Monoclonal Antibodies: Principle and Practice, pp. 59-103, (Academic Press, 1986).
Munson et al., "Ligand: A Versatile Computerized Approach for Characterization of Ligand-Binding Systems", Analytical Biochemistry, vol. 107, pp. 220-239, (1980).
Alausa, "The Use of Ammonium Sulphate Precipitation Method for the Determination of Antigen-Binding Capacity and Affinity of Anti-Tetanus Antibodies in Human Serum", Journal of Immunological Methods, vol. 8, pp. 117-126, (1975).
Keydar et al., "Production and characterization of monoclonal antibodies identifying breast tumor-associated antigens", Proc. Natl. Acad. Sci. USA, vol. 86, pp. 1362-1366, (1989).
Watier et al., "Removal of Terminal α-Galactosyl Residues from Xenogeneic Procine Endothelial Cells: Decrease in Complement-Mediated Antibody-Dependent Cell-Mediated Cytotoxicity1", Transplantation, vol. 62, No. 1, pp. 105-113, (1996).
Chuntharapai et al., "Isotype-Dependent Inhibition of Tumor Growth In Vivo by Monoclonal Antibodies to Death Receptor 4", J Immunol, vol. 166, pp. 4891-4898, (2001).
Kovjazin et al., "ImMucin: A novel therapeutic vaccine with promiscuous MHC binding for the treatment of MUC1-expressing tumors", Vaccine, vol. 29, pp. 4675-4686, (2011).
Correa et al., "Responses of human T cells to peptides flanking the tandem repeat and overlapping the signal sequence of MUC1", Int. J. Cancer, vol. 115, pp. 760-768, (2005).
Cohen et al., "Direct Detection and Quantitation of a Distinct T-Cell Epitope Derived from Tumor-specific Epithelial Cell-associated Mucin Using Human Recombinant Antibodies Endowed with the Antigen-specific, Major Histocompatibility Complex-restricted Specificity of T Cells", Cancer Research, vol. 62, pp. 5835-5844, (2002).
Harboe et al., "Generation of Antibodies to the Signal Peptide of the MPT83 Lipoprotein of *Mycobacterium tuberculosis*", Scand. J. Immunol., vol. 55, pp. 82-87, (2002).
Bar-Sinai et al., "Mouse Mammary Tumor Virus Env-Derived Peptide Associates with Nucleolar Targets in Lymphoma, Mammary Carcinoma, and Human Breast Cancer", Cancer Res, vol. 65, pp. 7223-7230, (2005).
Jiang et al., "Role of Signal Sequence in Vaccine-Induced Protection against Experimental Coccidioidomycosis", Infect. Immun., vol. 70, No. 7, pp. 3539-3545, (2002).
McMurry et al., "Analyzing *Mycobacterium tuberculosis* proteomes for candidate vaccine epitopes", Tuberculosis, vol. 85, pp. 95-105, (2005).
Mahanta et al., "A Minimal Fragment of MUC1 Mediates Growth of Cancer Cells", PLoS One, vol. 3, Issue 4, pp. e2054 (12 pages), (2008).
Kovjazin et al., "Autoantibodies against the signal peptide domain of MUC1 in patients with multiple myeloma: Implications for disease diagnosis and prognosis", Experimental and Therapeutic Medicine, vol. 3, pp. 1092-1098, (2012).
Pichinuk et al., "Antibody Targeting of Cell-Bound MUC1 SEA Domain Kills Tumor Cells", Cancer Res, vol. 72, pp. 3324-3336, (2012).
The International Search Report and Written Opinion for corresponding International Application No. PCT/IL2012/050365, 18 pages, mailed Mar. 25, 2013.

\* cited by examiner

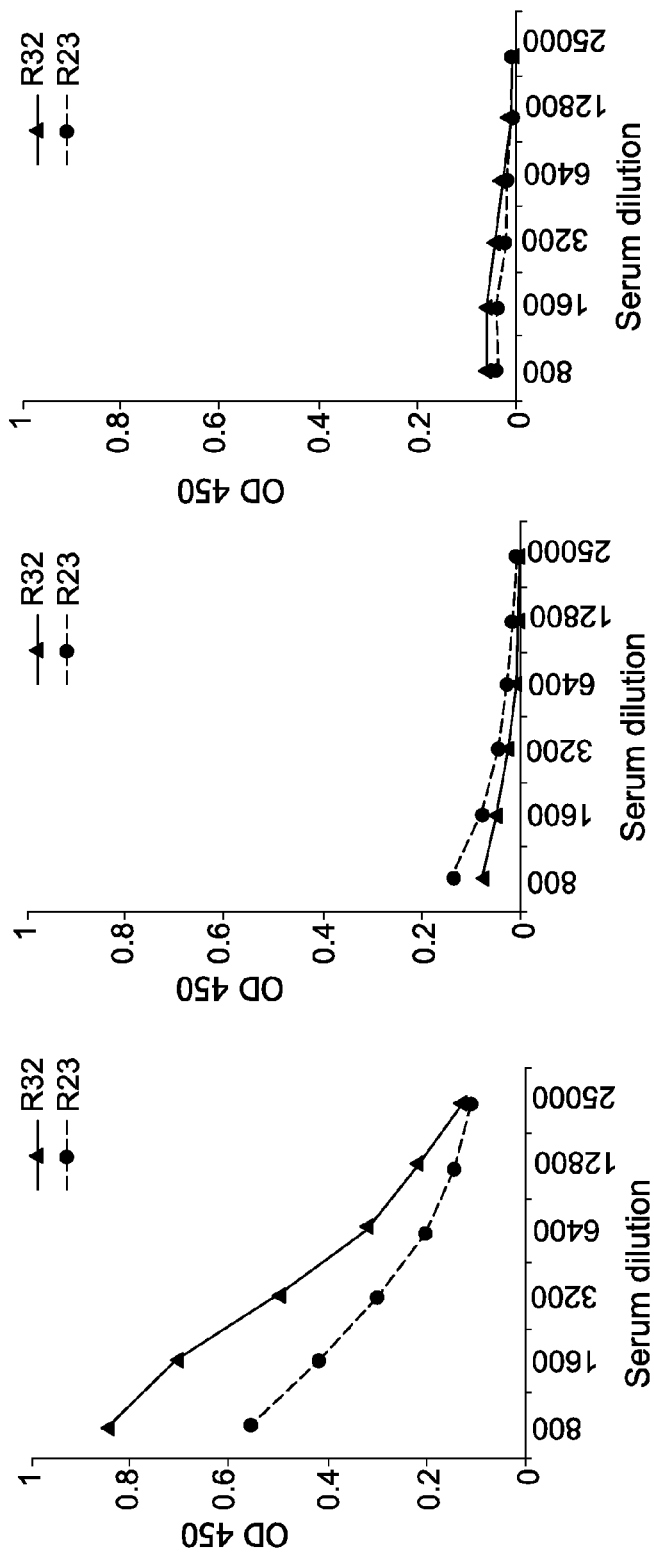

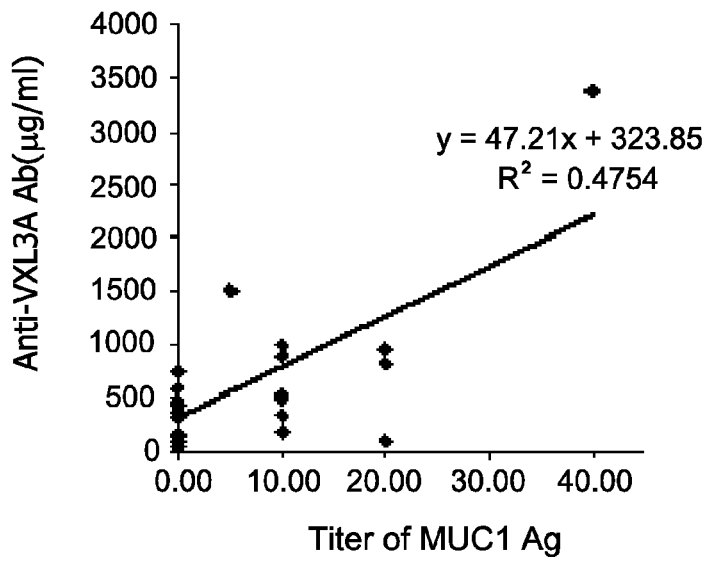
Fig. 7A
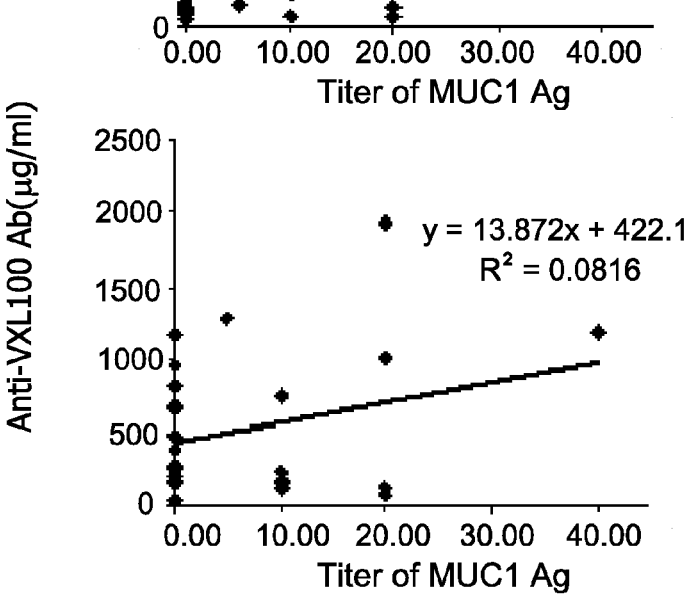
Fig. 7B
Fig. 7C

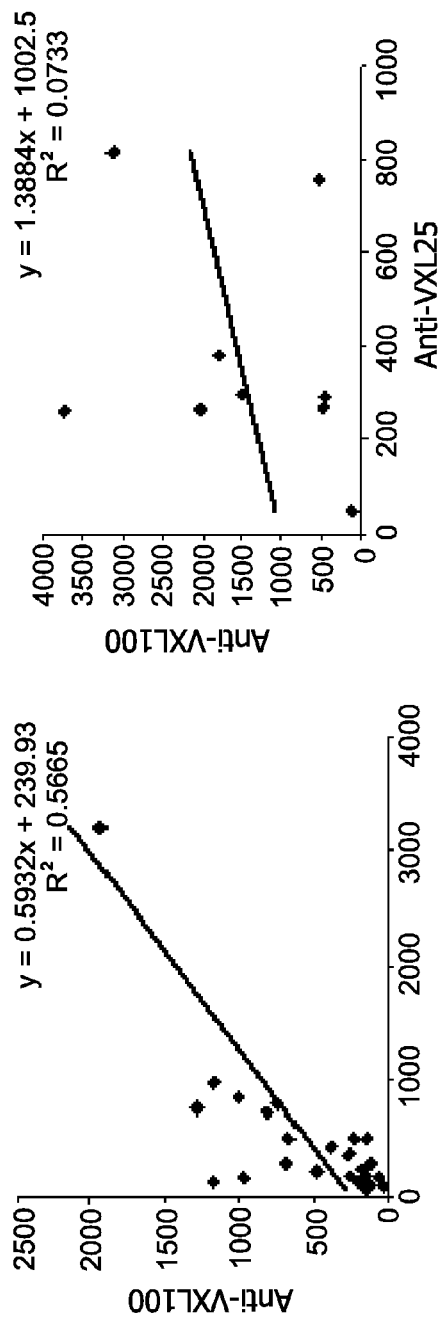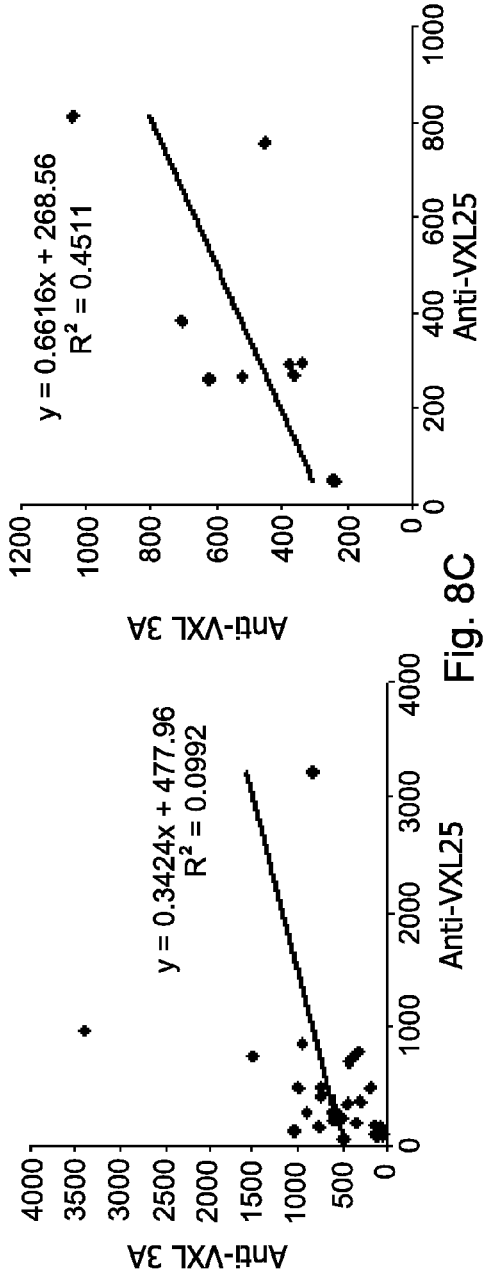
Fig. 8A  Fig. 8B  Fig. 8C  Fig. 8D

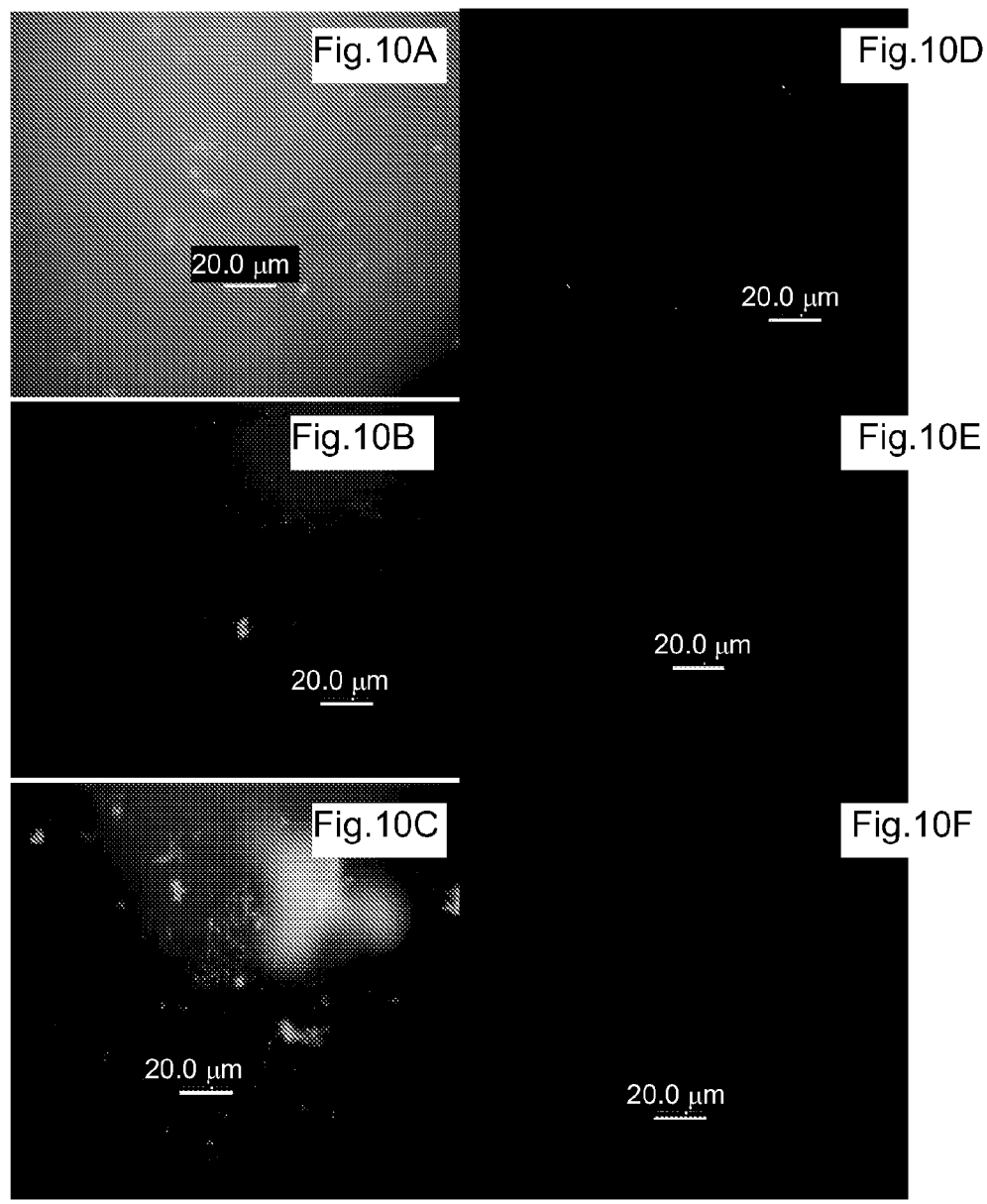

US 9,732,153 B2

ANTIBODIES DIRECTED AGAINST SIGNAL PEPTIDES, METHODS AND USES THEREOF

The Sequence Listing submitted in text format (.txt) filed on Mar. 13, 2014, named "SequenceListing.txt", created on Mar. 12, 2014, 4.87 KB), is incorporated herein by reference.

TECHNOLOGICAL FIELD

This invention relates to diagnostic and therapeutic methods employing antibodies directed against the signal peptide (SP) of disease-related polypeptides, in particular for the diagnosis and treatment of cancer and infectious diseases, specifically Tuberculosis.

BACKGROUND

In both prokaryotic and eukaryotic cells, proteins destined (or targeted) for secretion or for insertion into cellular membranes use short ~13-50 amino acids long, usually amino-terminal, signal peptides (SP), also termed signal sequences.

Different SPs of various antigens exhibit high sequence variability with no particular sequence identity while conforming to the motif needed to maintain their functionality (Lyko F. et al., *J Biol Chem* 1995, 270:19873-19878). Recently, SP and trans-membrane domains were found to have exceptionally high major histocompatibility complex (MHC) class I and II epitope densities. The improved MHC binding of these domains relies on their hydrophobic nature and, in SP, also on their specific sequence (Kovjazin, R. et al., Mol Immunol 2011, 48: 1009-1018).

The post targeting function of SP (Martoglio B. et al., Biochem Soc Trans 2003, 31:1243-1247), suggests that SP fragments may be directed to the cell membrane or to the extracellular compartment even without association with MHC molecules.

WO 2008/035350 relates to SP-derived vaccines, capable of inducing a robust, antigen specific T-cell immunity and which are applicable to the majority of the population.

Tumor associated antigens (TAA) are cancer associated epitopes or marker proteins. Many such antigens are known in the art, for example MUC1.

MUC1, the polymorphic epithelial mucin, is a glycoprotein with few alternative splicing variants encoding for transmembranal and secreted/soluble products, both are expressed in a broad range of tumors (Graham, R. A. et al., *Cancer Immunol Immunother* 1996, 42:71-80 and Ho, S. B. et al., *Cancer Res* 1993, 53:641-651). MUC1 is one of the few known targets that are expressed in more than 90% of the common solid tumor cancers, which include, among others: Colon, Gastric, Lung, Renal Cell (RC), Transitional Cell (TC), Prostate, Pancreas, Breast, Ovary and Thyroid. It is also associated with many non-solid tumors among which: Lymphoma, Leukaemia and Multiple Myeloma (MM).

It has been shown that the copy number of MUC1 increases in primary invasive breast carcinomas compared with normal tissue in correlation with its protein expression (Lacunza, E. et al., *Cancer Genet Cytogenet* 2010, 201:102-110). Other to studies, mainly in MM, have demonstrated that MUC1 is expressed on the cell surface of most MM cell lines, bone marrow (BM) plasma cells derived from patients, and plasmacytomas (Treon, S. P. et al., *Blood* 2000, 96:3147-3153).

Soluble MUC1 (sMUC1) levels containing an extracellular tandem repeat array (TRA) were reported to correlate with tumor mass, as measured by FDA (US Food and Drug Administration) approved assays like CA15.3 in breast cancer, and/or CA27.29 in MM cancer (Croce, M. V. et al., *Breast Cancer Res Treat* 2003, 81:195-207 and Teron, S. P et al., Blood, 2000, 96: 3147-53). However, despite the wide tumor distribution of MUC1, use of the CA15.3 and CA27.29 markers is confined to monitoring the prognosis and response to treatment in patients with advanced breast cancer (Gion, M. et al Clin. Chem. (1999) 45:630-637) and it is not sensitive enough to be used for early diagnosis. In contrast, naturally generated autoantibodies to TAAs are detectable even before the tumor is clinically apparent (Lu H. et al J. Proteome Res. (2008) 7: 1388-1394).

The use of anti-MUC1 monoclonal antibodies, mostly directed against the extracellular IRA epitope, was also reported as an anti-cancer modality (Tang, C. K. et al., *Expert Rev Vaccines* 2008, 7:963-975). However, since these epitopes are not restricted to cell surface expression but are also expressed in the sera of patients, the use of these anti-MUC1 monoclonal antibodies for diagnosis and therapy may be of reduced potency.

EP 1137943 relates to an in vitro method for detecting the presence of a cancer associated marker protein in mammals, where the cancer associated marker may be, among others, a modified cancer-associated form of MUC1.

GENERAL DESCRIPTION

The present invention is based on the finding that antibodies that were generated against the signal peptide (SP) domain of disease-associated polypeptides were capable of detecting cell surface expression of these SP domains in cancer cells or bacterial cells.

Therefore, in a first of its aspects, the present invention provides a method for determining the suitability for treatment of a subject suffering from a disease, the method comprises:
  a. contacting a biological sample containing cells obtained from said to subject with an antibody directed against a signal peptide (SP), or any fragment thereof, of a polypeptide associated with said disease; and
  b. determining the expression level of said SP, or any fragment thereof, on the surface of cells in said biological sample,
wherein the presence of said SP, or any fragment thereof, on the surface of said cells in a level higher than a control level indicates that said subject is suitable for treatment.

In another aspect, the present invention provides a method of treatment of a subject suffering from a disease, the method comprises administering to said subject a therapeutically effective amount of at least one antibody directed against a signal peptide (SP), or any fragment thereof, of a polypeptide associated with said disease.

In yet another aspect, the present invention provides a method of diagnosing a disease in a subject, the method comprises:
  a. contacting a biological sample containing cells obtained from said subject with an antibody directed against a signal peptide (SP), or any fragment thereof, of a polypeptide associated with said disease; and
  b. determining the level of said SP, or any fragment thereof, on the surface of cells in said biological sample,
wherein the presence of a level of said SP in said sample which is higher than a control level is indicative of a disease.

In yet another aspect, the present invention provides an isolated antibody directed against a signal peptide (SP), or any fragment thereof, of a polypeptide associated with a disease, for use in a method of determining the suitability for treatment of a subject suffering from said disease, wherein said method comprises:
 a. contacting a biological sample containing cells obtained from said subject with said isolated antibody; and
 b. determining the expression level of said SP, or any fragment thereof, on the surface of cells in said biological sample, wherein the presence of said SP, or any fragment thereof, on the surface of said cells in a level higher than a predetermined baseline indicates that said subject is suitable for treatment.

In yet another aspect, the present invention provides an isolated antibody directed against a signal peptide (SP), or any fragment thereof, of a polypeptide associated with a disease, for use in a method of treatment of a subject suffering from said disease, wherein said method comprises administering a therapeutically effective amount of said antibody to the subject.

In yet another aspect, the present invention provides an isolated antibody directed against a signal peptide (SP), or any fragment thereof, of a polypeptide associated with a disease for use in a method of diagnosing a disease in a subject, said method comprises:
 a. contacting a biological sample containing cells obtained from said subject with said isolated antibody; and
 b. determining the level of said SP, or any fragment thereof, on the surface of cells in said biological sample, wherein the presence of a level of said SP in said sample which is higher than a predetermined baseline level is indicative of a disease.

In yet another aspect, the present invention provides a method for detecting a disease in a subject, said method comprises:
 a. contacting a biological sample obtained from said subject with at least one SP, or any fragment thereof, of polypeptide associated with said disease; and
 b. measuring the level of endogenous antibodies directed against said SP, or any fragment thereof, in said biological sample, wherein the presence of said endogenous antibodies in the sample in a level higher than a control is indicative of disease.

In one embodiment, said disease is cancer.

In another embodiment, said disease is a bacterial disease, a fungal disease, a parasite disease, a prion disease, or a viral disease.

In one embodiment, the polypeptide associated with said disease is a Tumor associated antigen (TAA).

In specific embodiments, said TAA is selected from a group consisting of MUC1, Armet, HSP60, CANX, MTHFD2, FAP, MMP6, BAGE-1, GNTV, Q5H943, CEA, Pmel, Kallikrein-4, Mammaglobin-1, MART-1, GPR143-OA1, PSA, TRP1, Tyrosinase, FGP-5, NEU proto-oncogene, Aft, MMP-2, PSMA, Telomerase-associated protein-2, PAP, Uroplakin II and Proteinase 3.

In one specific embodiment, said TAA is MUC1.

In yet another specific embodiment, the polypeptide associated with said disease is MUC1 and said SP, or any fragment thereof, is a peptide selected from a group consisting of the peptides denoted by SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, and SEQ ID NO. 10.

In certain embodiments, said cancer is selected from a group consisting of multiple myeloma (MM), breast cancer, ovary cancer, colon cancer, rectal cancer, gastric cancer, non-small lung carcinoma (NScLC), renal cell carcinoma (RCC), transitional cell carcinoma (TCC), prostate cancer, pancreatic cancer, thyroid cancer, Squamous cell carcinoma (SCC), Thymic Carcinoma, lymphoma, leukemia, and Mesothelioma.

In a specific embodiment, said cancer is multiple myeloma (MM), breast cancer or ovarian cancer.

In yet another embodiment, the disease is a bacterial disease caused by *Mycobacterium tuberculosis* (MTb).

In specific embodiments, the polypeptide associated with the bacterial disease caused by *Mycobacterium tuberculosis* (MTb) is selected from the group consisting of Antigen 85B, Lipoprotein IpqH, ATP dependent helicase putative, Uncharacterized protein Rv0476/MTO4941 precursor and Uncharacterized protein Rv1334/MT1376 precursor.

In certain embodiments the antibody used in the methods of the invention is selected from a group consisting of a polyclonal antibody, a monoclonal antibody, a chimeric antibody, a humanized antibody, a human antibody, or any fragment thereof, which retains the binding activity of the antibody.

In specific embodiments said antibody is the polyclonal antibody R23 or its immunoglobulin enriched fraction R23IgG (also termed SPImAb-3A), the monoclonal antibody SPmAb-2.1 or the monoclonal antibody SPmAb-6 deposited at the ECACC on Sep. 13, 2012 under Accession no. 12091301.

In one embodiment, the present invention provides a method for determining the suitability for treatment of a subject suffering from a disease, as described above, wherein said treatment comprises at least one of a vaccine capable of eliciting an immune response against said SP, or any fragment thereof and an agent capable of binding said SP, or any fragment thereof.

In one embodiment, said agent is at least one of an antibody, a ligand, or any fragment thereof which is capable of binding the SP expressed on said cells.

In one specific embodiment, the polypeptide associated with said disease is MUC1 and said vaccine capable of eliciting an immune response is a therapeutic vaccine comprising MUC1 SP.

In certain embodiments the methods of determining the suitability for treatment of a subject suffering from a disease or the methods of diagnosis of the invention described above are performed ex vivo.

In certain embodiments the biological sample used in these methods is selected from a group consisting of plasma, serum, whole blood, urine, sweat, lymph, faeces, cerebrospinal fluid, bone marrow biopsy or aspirate, or nipple aspiration.

In one embodiment the method of treatment of a subject suffering from a disease according to the invention as described above the antibody is a neutralizing antibody.

In yet another embodiment, the antibody is associated with or combined with a cytotoxic moiety.

In specific embodiments, said cytotoxic moiety is selected from a group consisting of a radioactive agent, a toxin, an anti-metabolite, or an alkylating agent.

In yet another aspect, the present invention provides a kit comprising:

(a) an isolated antibody directed against a signal peptide (SP), or any fragment thereof, of a polypeptide associated with a disease;
(b) means for detecting the binding of said isolated antibody on the surface of cells in a biological sample obtained from a subject; and optionally further comprising
(c) instructions for use of said kit.

In certain embodiments said kit further comprises a vaccine comprising the signal peptide, or a fragment thereof capable of eliciting an immune response, of said polypeptide associated with a disease.

In certain embodiments, said means comprises
(a) a detectably-labeled secondary antibody which recognizes the anti SP antibody; and
(b) optionally further comprising reagents for performing said selection.

In one specific embodiment, said isolated antibody is directed against MUC1 SP.

In another specific embodiment, said isolated antibody is directed against the SP of a polypeptide of *Mycobacterium tuberculosis*.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 shows characteristics of antibodies that were generated against the SP domain of MUC1. FIGS. 1AI-1AIII show polyclonal antibody titers in sera obtained from two immunized rabbits, R23 and R32. Various serum dilutions are presented. Anti MUC1-SP-M is shown in FIG. 1AI; anti-BAGE-SP-L in FIG. 1AII; and anti TB-Rv0476/4941-SP-L in FIG. 1AIII.

FIG. 7A-7F is a graphical representation of the levels of sMUC1 (MUC1 Ag) as compared with the levels of endogenously generated antibodies against VXL3A, VXL25 and VXL100 in cancer patients having non-solid tumors (MM, FIG. 7, A-C) and for cancer patients having solid tumors, in particular Colon, Rectal, Lung, and Prostate (FIG. 7, D-F).

FIG. 8A-8D is a graphical representation of the intercorrelation of the concentrations of various endogenously generated anti-MUC1 peptide antibodies in MM patients (FIG. 8, A and B) and in patients with solid tumors (FIG. 8, C and D).

FIG. 10A-C shows photographs of 4'-6-Diamidino-2-phenylindole (DAPI) DNA staining of MTb bacteria. FIG. 10D is a photograph showing immunofluorescence staining of MTb bacteria with anti SP antibodies. FIG. 10E is a photograph showing immunofluorescence staining of a related mycobacterium strain, *M. Kansasii*. FIG. 10F is a photograph showing immunofluorescence staining of MTb bacteria with sera from normal mice.

DETAILED DESCRIPTION OF EMBODIMENTS

Figure 1B:
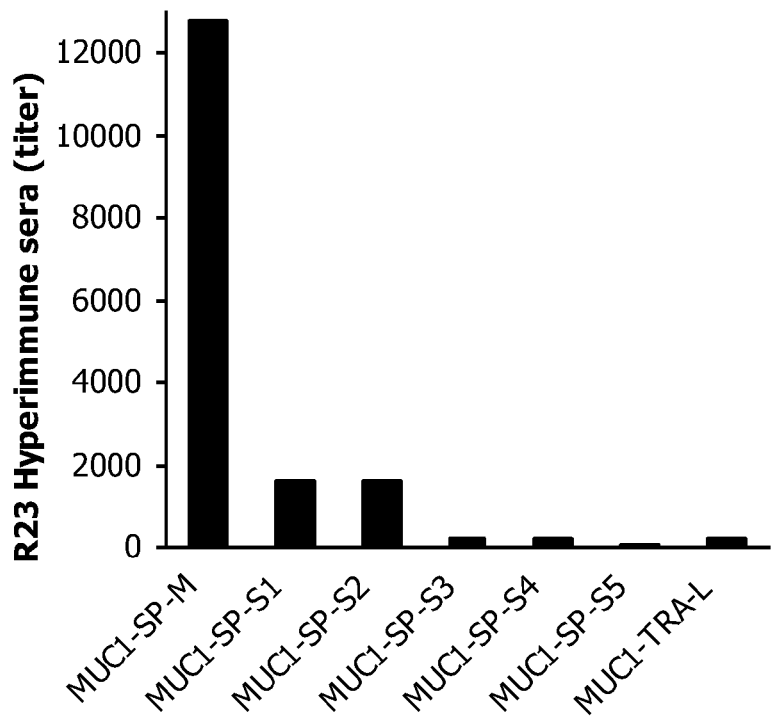
FIG. 1B is a graph showing the titer of R23 antibodies directed against various MUC1 epitopes.

The present invention is based on the surprising finding that signal peptide (SP) domains of disease-associated polypeptides are presented on the cell surface of cells.

Moreover, the inventors demonstrate that antibodies directed against the signal peptide (SP) domain of disease-associated polypeptides are capable of detecting cell surface associated expression of these SP domains in patients suffering from various diseases such as cancer or infectious diseases, e.g. *Mycobacterium tuberculosis*.

The present invention therefore provides methods of diagnosing and/or treating various diseases using antibodies directed against the signal peptide (SP) domain of disease-associated polypeptides.

The present invention also provides methods of diagnosing diseases by determining the level of endogenous antibodies (also termed "autoantibodies") which are produced by the patient and are directed against the signal peptide (SP) domain of disease-associated polypeptides.

Since the antibodies of the invention detect cell surface expression of the SP domain of a certain disease-associated polypeptide, they may be used as a tool for selecting patients suitable for treatment which is specifically directed against that SP domain.

As a non limiting example, if a patient is found to express on the cell surface of a tumor cell the SP domain of a disease associated polypeptide such as MUC1, such a patient is likely to benefit from therapy which is directed against MUC1 SP domain. Non limiting examples of such therapy are a vaccine comprising the MUC1 SP domain, e.g. ImMucin and/or antibodies which are directed against the MUC1 SP domain. Such antibodies may optionally be conjugated with cytotoxic moieties which facilitate cancer cell lysis.

Accordingly, by a first of its aspects, the present invention provides a method for determining the suitability for treatment of a subject suffering from a disease, the method comprises:
a. contacting a biological sample containing cells obtained from said subject with an antibody directed against a signal peptide (SP), or any fragment thereof, of a polypeptide associated with said disease; and
b. determining the expression level of said SP, or any fragment thereof, on the surface of cells in said biological sample,
wherein the presence of said SP, or any fragment thereof, on the surface of said cells in a level higher than a control level indicates that said subject is suitable for treatment.

As used herein the term "treatment" refers to clinical intervention in an attempt to alter the course of disease in the individual being treated, and can be performed either for prophylaxis or during the course of clinical pathology. Desirable effects of treatment include preventing occurrence or recurrence of the disease, alleviation of symptoms, reducing a pathological consequence of the disease, reducing the rate of disease progression, amelioration of the disease state, remission or improved prognosis. The term "treatment" may also encompass ex vivo procedures affecting cells or tissues in culture.

As used herein the term "subject" refers to an individual, or a patient, which is a vertebrate, e.g. a mammal, including especially a human.

As used herein the term "disease" refers to any condition which ameliorates the health of an individual. In one embodiment the present invention concerns a method for determining the suitability for treatment of a subject suffering from cancer. In other embodiments the present invention concerns a method for determining the suitability for treatment of a subject suffering from an infectious disease.

As used herein the term "cancer" refers to the physiological condition in mammals that is typically characterized by unregulated cell growth/proliferation. The term cancer also refers to cancer cells.

As used herein, the term "polypeptide associated with a disease" or "disease associated polypeptide" refers to proteins whose expression is highly correlated with the presence of certain diseases. These proteins are not usually expressed in normal cells, or are expressed at a higher extent in diseased cells than in normal cells. Specific, non limiting examples of disease associated polypeptides are, for example "TAA".

As used herein, the term "tumor associated antigen" or "TAA" refers to antigens or proteins that are highly correlated with certain tumor cells. These antigens are not usually expressed in normal cells, or are expressed at a higher extent in tumor cells than in normal cells. "TAA" also refers to cancer associated epitopes, cancer associated marker proteins, cancer associated proteins, or to a cancer marker. As used herein, the term "tumor associated antigen fragment" refers to antigenic fragment that is recognizable by an antibody directed against said tumor associated antigen.

Preferably, the disease associated polypeptide is expressed on the cell surface and is amenable to recognition by elements of the immune system such as immune cells or antibodies.

Specific, non limiting examples of TAAs include MUC1, Armet, HSP60, to CANX, MTHFD2, FAP, MMP6, BAGE-1, GNTV, Q5H943, CEA, Pmel, Kallikrein-4, Mammaglobin-1, MART-1, GPR143-OA1, PSA, TRP1, Tyrosinase, FGP-5, NEU proto-oncogene, Aft, MMP-2, PSMA, Telomerase-associated protein-2, PAP, Uroplakin II and Proteinase 3.

In certain embodiments the present invention concerns a method for determining the suitability for treatment of a subject suffering from a MUC1 expressing cancer. As used herein the terms "MUC1", "MUC1 antigen", "MUC1 Ag", or "MUC1 epitope" are used interchangeably and refer to a high molecular weight glycoprotein expressed on many cancer cell types. As used herein the term "MUC1 expressing cancer" refers to cancers expressing MUC1, which may be, but are not limited to multiple myeloma (MM), breast cancer, ovary cancer, colon cancer, rectal cancer, gastric cancer, non-small lung carcinoma (NScLC), renal cell carcinoma (RCC), transitional cell carcinoma (TCC), prostate cancer, pancreatic cancer, thyroid cancer, Squamous cell carcinoma (SCC), Thymic Carcinoma, lymphoma, leukemia, and Mesothelioma.

Methods for determining whether a cancer type or a cancer cell over-expresses MUC1 are well known in the art, and generally include detection of the MUC1 protein or mRNA encoding for the MUC1 protein.

As used herein the term "infectious disease" relates to a disease mediated by an infectious agent. Such agents may include viruses, bacteria, parasites, prions and fungi. Hence, the term "polypeptide associated with a disease" also encompasses polypeptides associated with infectious agents causing an infectious disease.

In one specific embodiment the infectious agent is *Mycobacterium tuberculosis* (MTb). In accordance with the invention, non limiting examples of polypeptides associated with MTb include Antigen 85B, Lipoprotein IpqH, ATP dependent helicase putative, Uncharacterized protein Rv0476/MTO4941 precursor and Uncharacterized protein Rv1334/MT1376 precursor.

As used herein the term "biological sample" includes, but is not limited to, plasma, serum, whole blood, urine, sweat, lymph, faeces, cerebrospinal fluid, bone marrow biopsy or aspirate, nipple aspiration or other biological sample derived from a subject.

As used herein the term "signal peptide" (SP) refers to a short (15-60 amino acids long) peptide chain that directs the transport of a protein. Signal peptides are also referred to as "targeting signals", "signal sequences", "transit peptides", or "localization signals". The invention encompasses both SP expressed on the cell surface of cells or to soluble SP, as well as to peptide fragments thereof.

A "fragment of an SP" as used herein is defined as any peptide fragment of a SP which is recognizable by a binding agent, e.g. an antibody. In certain embodiments, for epitope recognition in the context of MIIC class I, said fragment may be 9 amino acids long and for MHC class II, 15 amino acids long. The epitopes may be linear or conformational epitopes. In certain specific embodiments, the fragment comprises the C-terminus of the SP. The "C-terminus" (also known as the carboxyl-terminus, carboxy-terminus, C-terminal tail, C-terminal end, or COOH-terminus) refers to the end of the SP amino acid chain terminated by a free carboxyl group (—COOH), and may comprise one or more amino acids at the C-terminus. In certain embodiments an amide is used at the C terminus.

Identifying SP sequences for a particular disease-associated polypeptide may be performed by using any appropriate method known in the art. In particular, SP sequences may be identified using computer software, e.g. the signal P 3.0. The signal P 3.0 program uses both a neural network (NN) algorithm and a hidden Markov Models (HMM) algorithm for selection of the signal sequence. In certain embodiments, the epitopes in accordance with the invention may be an incomplete SP. For example, without wishing to be bound by theory, the C-terminal of the SP may be more relevant for cellular interaction as it is probably the part that gets to the surface without the MHC. A sequence is considered to be a SP whenever a score of over 0.2 was received in one or more of the algorithms. Sequences having a score of above 0.7 are preferred. Sequences having a score of above 0.8 are most preferred.

Examples of SP sequences are provided in Table 1 below, and include VXL100 which consists of the entire MUC1SP domain, and shorter peptides which correspond to MUC1 SP fragments, e.g. VXL3A, VXL1, VXL2, VXL3, VXL4, VXL5, VXL13 and VXL15. The table also shows the SP of the TAAs Armet (VXL101), BAGE (VXL102), Uroplakin II (VXL104), PAP (VXL106) and Mammaglobin-1 (VXL108), as well as the SP sequences of several MTb proteins including Ag85B (VXL201), Lipoprotein lpqH (VXL203), ATP dependent helicase putative protein (VXL208), Uncharacterized protein Rv0476/MTO4941 precursor (VXL211), and Uncharacterized protein Rv1334/MT1376 precursor (VXL212).

TABLE 1

List of sequences

| SEQ ID NO. | Sequence | Name | Description |
|---|---|---|---|
| 1 | STAPPAHGVTSAPDTRPAPGSTAPP | VXL25, BP25 or MUC1-TRA-L | A peptide derived from the TRA domain of human MUC1. |
| 2 | MTPGTQSPFFLLLLLTVLTVV | VXL100 or MUC1-SP-L | A peptide consisting of the entire domain of human MUC1 SP. VXL100 is the antigenic portion (API) of the vaccine ImMucin. |
| 3 | KKFLLLLLTVLTVVKKK | VXL3A or MUC1-SP-M | A peptide which consists of the fragment 10-21 of human MUC1 SP and includes five additional lysines at the N- and C-terminal. |
| 4 | LLLTVLTVV | VXL1, MUC1-SP-S1 or MUC1D6 | A peptide which consists of the fragment 13-21 in human MUC1 SP. |
| 5 | LLLLTVLTV | VXL2, MUC1-SP-S2 or MUC1C6 | A peptide which consists of the fragment 12-20 in human MUC1 SP. |
| 6 | FLLLLLTVL | VXL3 or MUC1-SP-S3 | A peptide which consists of the fragment 10-18 of human MUC1 SP. |
| 7 | TQSPFFLLL | VXL4 or MUC1-SP-S4 | A peptide which consists of the fragment 5-13 in human MUC1 SP. |
| 8 | SPFFLLLLL | VXL5 or MUC1-SP-S5 | A peptide which consists of the fragment 7-15 in human MUC1 SP. |
| 9 | FFLLLLLTV | VXL13 | A peptide which consists of the fragment 9-17 in human MUC1 SP. |
| 10 | MTPGTQSPF | VXL15 | A peptide which consists of the fragment 1-9 in human MUC1 SP. |
| 11 | MWATQGLAVALALSVLPGSRA | VXL101 | A peptide which consists of the entire SP domain of the human protein Armet. |
| 12 | MAARAVFLALSAQLLQA | VXL102 or BAGE-SP-L | A peptide which consists of the entire SP domain of the human protein BAGE. |
| 13 | MAPLLPIRTL PLILILLALL SPGAA | VXL104 | A peptide which consists of the entire SP domain of the human TAA Uroplakin II. |
| 14 | MFDKTRLPYVALDVLCVLLAGLPFAIL | VXL106 | A peptide which consists of the entire SP domain of the human TAA PAP. |
| 15 | MKLLMVLMLAALSQHCYA | VXL108 | A peptide which consists of the entire SP domain of the human TAA Mammaglobin-1. |

TABLE 1-continued

List of sequences

| SEQ ID NO. | Sequence | Name | Description |
|---|---|---|---|
| 16 | MTDVSRKIRAWGRRLMIGTAAAVVL PGLVGLAGGAATAGA | VXL201 | A peptide which consists of the entire SP domain of the Mycobacterium tuberculosis protein Ag85B. |
| 17 | MKRGLTVAVAGAAILVAGLSGCSS | VXL203 | A peptide which consists of the entire SP domain of the Mycobacterium tuberculosis protein Lipoprotein IpqH. |
| 18 | MRFAQPSALSRFSALTRDWFTSTFAA PTAAQA | VXL208 | A peptide which consists of the entire SP domain of the Mycobacterium tuberculosis ATP dependent helicase putative protein. |
| 19 | MLVLLVAVLVTAVYAFVHA | VXL211 or TB-Rv0476/ 4941-SP-L | A peptide which consists of the entire SP domain of the Mycobacterium tuberculosis protein Uncharacterized Rv0476/MTO4941 precursors. |
| 20 | MLLRKGTVYVLVIRADLVNAMVAHA | VXL212 | A peptide which consists of the entire SP domain of the Mycobacterium tuberculosis protein uncharacterized Rv1334/1376. |

In accordance with the invention the SP domain of a desired disease associated polypeptide is used for the preparation of specific antibodies, i.e. anti SP antibodies. Such antibodies may be used in the method for determining the suitability for treatment of a subject suffering from a disease as well as in additional aspects of the invention as would be discussed below.

The terms "antibody" and "immunoglobulin" are used interchangeably in the broadest sense and specifically refer to a polyclonal antibody, a monoclonal antibody, or any fragment thereof, which retains the binding activity of the antibody. In certain embodiments the use of a chimeric antibody, a humanized antibody, or a human antibody is also encompassed by the invention.

As used herein the term "polyclonal antibody (or antibodies)" refers to a population of different antibodies directed against different determinants (epitopes) of the same antigen.

The term "monoclonal antibody (or antibodies)" as used herein refers to a population of substantially homogenous antibodies, i.e., the individual antibodies comprising the population are identical except for possibly naturally occurring mutations that may be present in minor amounts. Monoclonal antibodies are directed against a single antigenic site.

The anti SP monoclonal antibodies of the invention can be made using the hybridoma method first described by Kohler et al, Nature, 256: 495 (1975), or may be made by recombinant DNA methods (e.g. U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to the SP generally are raised in animals by subcutaneous (sb) or intraperitoneal (ip) injections of the desired SP (for example SP domains listed in Table 1) and an adjuvant. In one embodiment, the animals are immunized with the SP coupled to Keyhole limpet hemocyanin (KLH, Sigma Aldrich) as a carrier protein.

The signal peptides used for animal immunization are prepared using methods well-known in the art. For example, the SP may be produced by recombinant methods or by peptide synthesis methods.

Alternatively, lymphocytes may be immunized in vitro and then fused with myeloma cells using a suitable fusing agent, such as polyethylene glycol, to form a hybridoma cell (Goding, Monoclonal Antibodies: Principles and Practice, pp. 59-103 (Academic Press, 1986)).

The binding affinity of the monoclonal antibody can, for example, be determined by the Scatchard analysis of Munson et al., Anal Biochem., 107: 220 (1980).

The anti SP antibodies of the invention can be made by using combinatorial libraries to screen for synthetic antibody clones with the desired activity. In principle, synthetic antibody clones are selected by screening phage libraries containing phage that display various fragments of antibody variable region (Fv) fused to phage coat protein using methods well known in the art.

As used herein the term "any fragment thereof which retains the binding activity of the antibody" refers to a portion of an antibody, preferably comprising the antigen-binding or variable region thereof, which is capable of binding to the target antigen of the intact antibody. Examples of antibody fragments include Fab, Fab', F(ab')$_2$, and Fv fragments.

These antibody fragments may be generated by recombinant techniques or by traditional means, such as enzymatic digestion. Papain digestion of antibodies produces two identical antigen-binding fragments, called "Fab" fragments, each with a single binding site, and a residual "Fc" fragment. Pepsin treatment yields an F(ab')$_2$ fragment that has two antigen-combining sites and is still capable of cross-linking antigen. "Fv" is the minimum antibody fragment which contains a complete antigen-recognition and binding site.

The polyclonal antibodies and the monoclonal antibodies of the invention are prepared using methods well known in the art.

A specific non limiting example of methods for preparing anti SP antibodies is provided in Example 1 below.

In specific embodiments, the antibodies used in the methods of the invention include the polyclonal preparations denoted R23 or R23IgG (which is an IgG fraction of rabbit's polyclonal hyper immune sera directed against the 17 amino acid long MUC1 SP peptide VXL3A (SEQ ID NO: 3)) or SPImAb-3A (which is an IgG fraction of rabbit's polyclonal hyper immune sera which is directed against the 21 amino acid long MUC1 SP peptide VXL100 (SEQ ID NO: 2)). In other embodiments the antibodies used in the methods of the invention include the monoclonal antibodies denoted SPmAb-2.1 and SPmAb-6. These monoclonal antibodies are directed against the 17 amino acid long MUC1 SP peptide VXL3A (SEQ ID NO: 3). The hybridoma cell producing the SPmAb-6 antibody was deposited at the ECACC on Sep. 13, 2012 and received Accession no. 12091301.

Interestingly, the polyclonal antibodies directed to the 17mer (17 amino acid long peptide) MUC1 SP were found to be more specific to the MUC1 SP Domain as compared with the polyclonal antibodies directed to the 21mer (21 amino acid long peptide) MUC1 SP.

The cell surface expression level of the SP of the disease associated polypeptide may be determined using the anti SP antibodies in any suitable detection method known in the art, for example, by employing ELISA, RIA, FACS analysis or immunohistochemistry.

The level of expression is measured and compared with the level of expression of a suitable control. A control may be the level of expression of a non-relevant SP (e.g. of a non-relevant TAA, or of a foreign antigen (of an infectious agent) such as an MTb), or the level of expression of the same SP on a normal, non diseased cell of the same or a different individual.

In one embodiment, "positive" is defined as having at least a double geometric mean of the control. In one embodiment, "negative" result in FACS analysis is defined as absence or <30% increase of the geometric mean in a sample stained with the evaluated Ab as compared with a sample stained with isotype control (e.g. normal mouse or rabbit polyclonal or monoclonal Abs FITC conjugated).

A subject is found to be suitable for treatment whereby cell surface expression of the SP (or the SP fragment) of the disease-associated polypeptide is detected.

In specific embodiments the treatment encompasses administering an agent which is specifically directed against the SP of the disease-associated polypeptide, i.e. an agent capable of binding to the SP. The term "an agent capable of binding" as used herein refers to an agent capable of binding an antigen with sufficient affinity such that the agent is useful as a therapeutic agent in targeting a cell expressing the antigen. Preferably, the agent is capable of causing (directly or indirectly) the destruction of cells harboring these SP domains.

Such agents may be, but are not limited to, a ligand, an antibody, a combination of antibodies, or any fragment thereof, capable of binding the SP domains. In one embodiment, binding of antibodies to cells via the SP domains may result in the selective elimination of such cells by the complement system.

In other specific embodiments the treatment encompasses administering a vaccine capable of eliciting an immune response against the SP, or any fragment thereof, thereby inducing the immune system of the subject to raise or enhance an immune response against the cells harboring the SP domains. As used herein, the term "vaccine" refers to a composition that improves immunity to a particular disease.

Examples of such vaccines may be found in WO 2008/035350 which relates to SP-derived vaccines, capable of inducing a robust, antigen specific T-cell immunity and which are applicable to the majority of the population.

In one specific embodiment the vaccine comprises a MUC1 SP, e.g. VXL100 or VXL3A, or a formulated version of the MUC1 SP, known as ImMucin. In other embodiments the treatment may include a combination of a MUC1 SP vaccine (e.g. ImMucin, VXL100 or VXL3A) and at least one anti MUC1 SP antibody.

Without wishing to be bound by theory, one advantage of such treatments is the relative low toxicity thereof, since these treatments are specifically directed to cells presenting the SP domains on their cell surface.

The treatment may include a combination of a vaccine and at least one antibody, or a combination of several antibodies with and without a vaccine. Specifically, the invention encompasses a therapeutic regime including a combination of a MUC1 SP vaccine (e.g. ImMucin) and anti MUC1 SP antibodies. The invention also encompasses a therapeutic regime including a combination of anti MUC1 SP antibodies together with additional agonistic antibodies directed against MUC1 or any other suitable TAA.

Since the antibodies of the invention detect cell surface but not soluble expression of the SP domain of a certain disease-associated polypeptide, they may be used as a therapeutic tool for selectively destroying cells which express these SP domains on their cell surface.

This effect may be mediated by activation of the complement system or by attaching a cytotoxic moiety to the anti SP antibodies.

As a non limiting example, antibodies directed against MUC1 SP domain may be used for causing cell death of MUC1 expressing cancer cells or in a method of treating MUC1 expressing cancers. The antibodies may optionally be conjugated with cytotoxic moieties which facilitate cancer cell lysis.

Accordingly, by a second of its aspects, the present invention provides a method of treatment of a subject suffering from a disease, the method comprises administering to said subject a therapeutically effective amount of at least one antibody directed against a signal peptide (SP), or any fragment thereof, of a polypeptide associated with said disease, whereby the binding of said antibody to cell surface expressed SP directly or indirectly results in cell death.

The invention also provides a method of inducing cell death or inhibiting cell growth, comprising administering to a population of cells at least one antibody directed against a signal peptide (SP), or any fragment thereof, of a polypeptide associated with said disease, whereby the binding of said antibody to cell surface expressed SP directly or indirectly results in cell death.

Optionally, the antibody is administered in combination or in association with a cytotoxic moiety.

As used herein the term "cytotoxic moiety" refers to a substance that inhibits or prevents the function of cells and/or causes destruction of cells. The term includes, for example, a radioactive agent, a toxin, an anti-metabolite, or an alkylating agent. The conjugation of the antibody with the cytotoxic moiety is performed using methods well known in the art.

The invention therefore also provides use of immune conjugates of the anti SP antibodies (i.e. antibody-drug conjugates), comprising any of the anti SP antibodies described herein conjugated to a cytotoxic agent such as a chemotherapeutic agent, a drug, a growth inhibitory agent, a toxin (e.g. an enzymatic active toxin of bacterial, fungal, plant or animal origin, or fragments thereof) or a radioactive isotope.

Optionally, the antibody mediates cell lysis via complement activation.

The term "a therapeutically effective amount" refers to an amount effective, at dosages and for periods of time necessary, to achieve the desired therapeutic or prophylactic result.

As used herein the term "cell death" refers to a viable cell which becomes nonviable, cell death may be caused by lysis, apoptosis or indirectly as a result of inhibition of cell proliferation or cell division (encompassing both a cytolytic and a cytostatic effect).

As used herein, the anti SP antibodies may be monoclonal or polyclonal antibodies as described above. In specific embodiments, the antibodies are non human antibodies e.g. mouse or rabbit antibodies. In other embodiments the anti SP antibodies are chimeric antibodies, or humanized antibodies or human antibodies.

As used herein the term "chimeric antibody" refers to antibodies in which a portion of the heavy and/or light chain is identical with or homologous to corresponding sequences in antibodies derived from a particular species or belonging to a particular antibody class or subclass, while the remaining chain(s) are identical with or homologous to corresponding sequences in antibodies derived from another species or belonging to another antibody class or subclass. For example, a chimeric antibody may include a human Fc portion and a mouse or rabbit variable region.

As used herein the term "humanized antibody" refers to antibodies which have a human backbone and contain minimal sequences (e.g. in the complementarity determining region, CDR) derived from non-human immunoglobulin.

A "human antibody" is an antibody which comprises an amino acid sequence corresponding to that of an antibody produced by a human and/or has been made using any of the techniques for making human antibodies known to those skilled in the art.

In one non limiting example, an amount of between 4 and 16 mg/Kg body weight of anti MUC1 SP antibodies (e.g. anti-VXL100 antibodies) are administered to an individual (for example by intra peritoneal, or intra venous injection) 1, 2 or 3 times at a weekly interval. The exact dosage form and regimen would be determined by the physician according to the patient's condition.

Since the antibodies of the invention detect cell surface expression of the SP domain of a certain disease-associated polypeptide, they may be used as a tool for diagnosing patients suffering from the disease. In such case the SP expression serves as a disease marker.

As a non limiting example, a biological sample obtained from an individual may be screened for cell surface expression of MUC1 SP. Expression of MUC1 SP may be indicative of disease, e.g. multiple myeloma. Preferably, the screening is performed with a combination of anti MUC1 SP antibodies with detectors of additional cell markers.

Accordingly, by another aspect, the present invention provides a method of diagnosing a disease in a subject, the method comprises:

a. contacting a biological sample containing cells obtained from said subject with an antibody directed against a signal peptide (SP), or any fragment thereof, of a polypeptide associated with said disease; and b. determining the level of said SP, or any fragment thereof, on the surface of cells in said biological sample, wherein the presence of a level of said SP in said sample which is higher than a control level is indicative of a disease.

The present invention also provides methods of diagnosing diseases by determining the level of endogenous antibodies (also termed "autoantibodies") which are produced by the patient and are directed against the signal peptide (SP) domain of disease-associated polypeptides.

Accordingly, by yet another aspect, the present invention provides a method for detecting a disease in a subject, said method comprises:

a. contacting a biological sample obtained from said subject with at least one SP, or any fragment thereof, of polypeptide associated with said disease; and b. measuring the level of endogenous antibodies directed against said SP, or any fragment thereof, in said biological sample, wherein the presence of said endogenous antibodies in the sample in a level higher than a control is indicative of disease As used herein the term "endogenous antibodies" refers to antibodies generated in a subject's body by its own immune system.

In accordance with this aspect of the invention the level of endogenous anti SP antibodies in a biological sample is determined by contacting the sample with a SP or a fragment thereof.

Methods for identifying SP domain sequences for use in accordance with the invention, were described above. Peptides based on these SP domains may be used for detecting anti SP endogenous antibodies present in the biological sample. The nomenclature used to describe peptide compounds of the invention follows the conventional practice wherein the amino group (N-terminus) is presented to the left and the carboxyl terminus (C-terminus) is presented to the right.

Derivative of the peptides are also included in the present invention. Derivatives are meant to include peptides which differ in one or more amino acids in the overall sequence, which have deletions, substitutions, inversions or additions. It is appreciated that these peptide modifications and peptide derivatives must not alter the structure of the original peptides in a manner that abrogates the ability of endogenous antibodies to recognize and bind these modified peptides.

The peptides according to the invention can be produced synthetically, or by recombinant DNA technology. Methods for producing peptides are well known in the art.

The level of binding of endogenous antibodies to the SP domains may be performed using any immunological technique known in the art. Particularly, the level of endogenous antibodies may be measured using ELISA, radioimmunoassay, or similar techniques.

Examples of methods for detecting anti SP endogenous antibodies are provided in the Examples below.

In a specific embodiment, the present invention provides a method of quantifying anti MUC1 SP autoantibodies using ELISA assays with MUC1 SP specific epitopes in the sera of multiple myeloma cancer patients. Interestingly, the level of such antibodies is significantly increased in MM patients as compared to healthy individuals thereby providing a tool for diagnosing the disease. Without wishing to be bound by theory, this significant increase stems chiefly from the preferred immunogenicity of the signal peptide.

Naturally generated autoantibodies to TAAs are detectable even before the tumor is clinically apparent (Lu H. et al J. Proteome Res. (2008) 7: 1388-1394), and due to their lower fluctuation and longer half-life in the blood, they may be more appropriate for cancer diagnosis than autoantibodies directed to non-SP domains of TAAs.

The present invention also provides specific antibodies directed to SP domains of peptides associated with a disease, or fragments thereof, for use in the above described methods for example to identify subjects that may benefit from or may be suitable to treatment as defined above.

Importantly, the antibodies of the invention may also be specifically used for treatment of subjects suffering from a disease. As a non limiting example, the antibody of the invention may be a neutralizing antibody, or an antibody associated with or combined with a cytotoxic moiety.

Therefore, in yet another aspect, the present invention provides an isolated antibody directed against a signal peptide (SP), or any fragment thereof, of a polypeptide associated with a disease, for use in a method of determining the suitability for treatment of a subject suffering from said disease, wherein said method comprises:
  c. contacting a biological sample containing cells obtained from said subject with said isolated antibody; and
  d. determining the expression level of said SP, or any fragment thereof, on the surface of cells in said biological sample,
wherein the presence of said SP, or any fragment thereof, on the surface of said cells in a level higher than a predetermined baseline indicates that said subject is suitable for treatment.

In yet another aspect, the present invention provides an isolated antibody directed against a signal peptide (SP), or any fragment thereof, of a polypeptide associated with a disease, for use in a method of treatment of a subject suffering from said disease, wherein said method comprises administering a therapeutically effective amount of said antibody to the subject.

In yet another aspect, the present invention provides an isolated antibody directed against a signal peptide (SP), or any fragment thereof, of a polypeptide associated with a disease for use in a method of diagnosing a disease in a subject, said method comprises:
  c. contacting a biological sample containing cells obtained from said subject with said isolated antibody; and
  d. determining the level of said SP, or any fragment thereof, on the surface of cells in said biological sample,
wherein the presence of a level of said SP in said sample which is higher than a predetermined baseline level is indicative of a disease.

An "isolated" antibody is one which has been identified and separated and/or recovered from a component of its natural environment.

EXAMPLES

Example 1

Generation of Antibodies Directed Against the SP Domain of MUC1

Animals used for producing antibodies were six to 8-week-old female BALB/c mice and two month old rabbits (the Tel-Aviv university breeding facility). Animals were maintained in the university animal research facility. All experiments were conducted according to the Tel-Aviv university institutional rules and regulations.

The peptides MUC1-SP-L (also referred to as VXL100 or denoted by SEQ ID NO.2), MUC1-SP-M (also referral to as VXL3A or denoted by SEQ ID NO.3), MUC1-SP-S1 (also referred to as VXL1, MUC1D6 or denoted by SEQ ID NO.4), MUC1-SP-S2 (also referred to as VXL2, MUC1C6 or denoted by SEQ ID NO.5), MUC1-SP-S3 (also referred to as VXL3 or denoted by SEQ ID NO.6), MUC1-SP-S4 (also referred to as VXL4 or denoted by SEQ ID NO.7), MUC1-SP-S5 (also referred to as VXL5, or denoted by SEQ ID NO.8) and TB-Rv0476/4941-SP-L (also referred to as VXL211, or denoted by SEQ ID NO.19) were synthesized by fully automated, solid-phase, peptide synthesis using fluorenylmethyloxycarbonyl (Fmoc)/tBu-strategy and Rink-amide-polystyrene resin at EMC Microcollections, Germany, while MUC1-TRA-L (also referred to as VXL25) and BAGE-SP-L were synthesized using the same methodology at GL Biochem, China. The purity and identity of all peptides was >95%, as determined by HPLC and MS analysis. Nomenclature used in selected peptide is as follows: "S" denotes short, "M" denotes moderate and "L" denotes long.

A 17mer SP domain of MUC1 (MUC1-SP-M peptide, also denoted by SEQ ID NO. 3, or VXL3A, Table 1) coupled to Keyhole limpet hemocyanin (KLH, Sigma Aldrich) as a carrier protein was used for generating polyclonal and monoclonal antibodies. The MUC1-SP-M peptide-KLH conjugation was prepared by cross linking with Glutaraldehyde by Adar biotech (Rehovot, Israel), according to methods well known in the art. MUC1-SP-M conjugated to KLH was emulsified with complete Freund's adjuvant in the first immunization and Incomplete Freund's adjuvant in subsequent immunizations.

Additional polyclonal antibodies were also generated against the 21 mer peptide derived from MUC1 SP (i.e., VXL100, also denoted by SEQ ID NO.2) using the same methods as described for the 17mer antigen, and termed SPImAb-3A.

Anti MUC1 SP Polyclonal Antibodies

Polyclonal antibodies were prepared as follows: Four 2 months old rabbits were subcutaneously immunized five times at weekly intervals. Samples were obtained from the immunized rabbits after each of the first three immunizations in order to check the titer quality. Then, two additional injections were administered at weekly intervals and the rabbits were boosted when a decline in the antibodies titer was observed.

After the final immunization (at day 58), rabbits sera were examined for the presence of specific antibodies directed against MUC1-SP-M (also termed VXL3A or denoted by SEQ ID NO.3), and positive sera (titer 1:12,500) were collected and pulled. For all immunological assays, an IgG fraction was used, following 40% ammonium sulfate precipitation as previously described in Alausa, O.K. [Journal of immunological methods. 8(1-2):117-126 (1975)].

Polyclonal Antibody Specificity

Titers of anti-MUC1-SP-M polyclonal antibody sera of up to 1: 12,800 dilutions were obtained in two of the immunized rabbits, namely R23 and R32 (FIG. 1AI). The polyclonal antibody preparations were accordingly denoted R23 and R32. In these experiments, an optical density (O.D.) larger than 0.1 (O.D. >0.1) was considered as a positive result. The specificity of the antibodies directed to MUC1 was high and showed limited cross reactivity with other SP domains (titers of <1:800), as shown in FIGS. 1AII and 1AIII: FIG. 1AII demonstrates a limited cross reactivity observed between the antibodies directed to MUC1 and the peptide BAGE-SP-L (also denoted by SEQ ID NO. 12, Table 1), which is derived from the eukaryotic protein BAGE, and FIG. 1AIII demonstrates a limited cross reactivity observed between the antibodies directed to MUC1 and the peptide TB-Rv0476/4941-SP-L (also denoted by SEQ ID NO. 19, Table 1), derived from the bacteria Mycobacterium tuberculosis.

As demonstrated in FIG. 1B, the inner epitopes of MUC1-SP-M which were highly recognized by the R23 antibodies were MUC1-SP-S1 (also denoted by SEQ ID NO.4, Table 1) and MUC1-SP-S2 (also denoted by SEQ ID NO.5, Table 1). These peptides are located at the C-terminus of MUC1 SP.

Figure 1C:
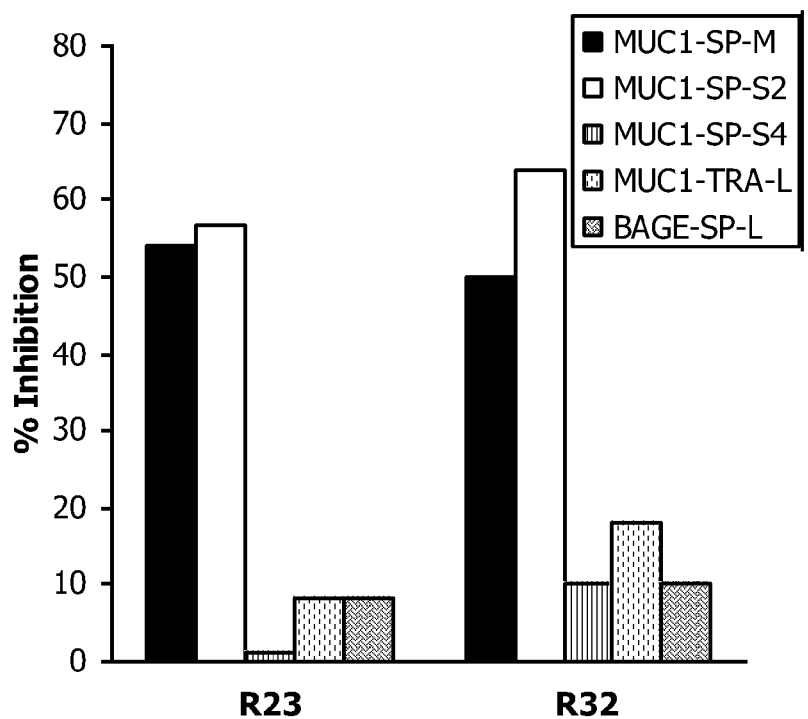
FIG. 1C is a graph showing % inhibition of binding of R23 and R32 polyclonal antibodies by various MUC1 and BAGE SP peptides.
Figure 1D:
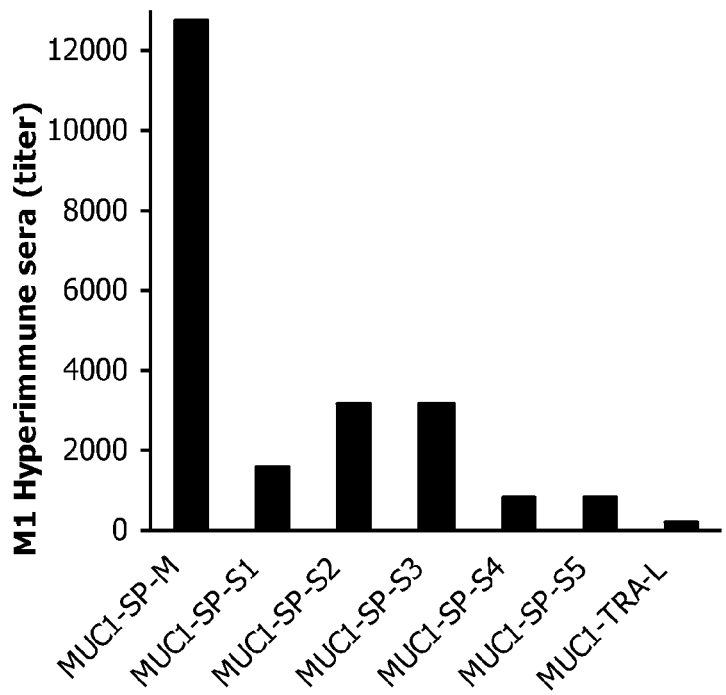
FIG. 1D is a graph showing the titer of antibodies in mouse hyperimmune sera directed against various MUC1 epitopes.
Figure 1E:
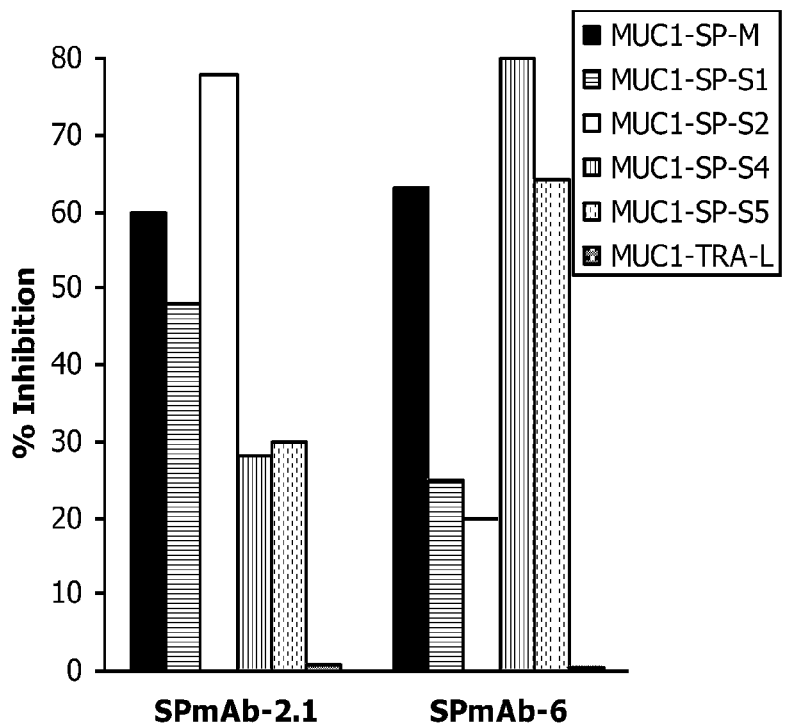
FIG. 1E is a graph showing % inhibition of binding of SPmAb-2.1 and SPmAb-6 monoclonal antibodies by various MUC1 SP peptides.

As demonstrated in FIG. 1C, over 50% inhibition was observed both for R23 and for R32 polyclonal antibodies by MUC1-SP-M (also denoted by SEQ ID NO.3) and its inner epitope MUC1-SP-S2 (also denoted by SEQ ID NO.5). However, less than 10% inhibition was achieved by other MUC1 SP epitopes, in particular MUC1-SP-S4 (also denoted by SEQ ID NO.7) and the MUC1 TRA epitope MUC1-TRA-L (also denoted by SEQ ID NO.1) or by the RAGE SP domain BAGE-SP-L (also denoted by SEQ ID NO.12).

Anti MUC1 SP Monoclonal Antibodies

Monoclonal antibodies were prepared as follows: Four BALB/c mice were subcutaneously immunized four times (at weekly intervals) with the MUC1-SP-M (also named VXL3A, or denoted by SEQ ID NO.3) peptide (100 µg) conjugated to KLH and emulsified in Complete Freund's adjuvant (CFA) at the first immunization and in Incomplete Freund's adjuvant (IFA) at the subsequent immunizations. After the final immunization step (two weeks), mice sera were examined for the presence of specific antibodies against MUC1-SP-M. Titers of anti-MUC1-SP-M polyclonal antibody sera of up to 1: 25,000 dilutions were obtained in the immunized mice. Spleen cells obtained from the mouse bearing the highest positive sera were harvested and fused with the murine myeloma partner NSO cell line, using polyethylene glycol (molecular weight 1500, Roche Diagnostics GmbH, Germany). Hybridomas cells were selected for two weeks in DMEM media supplemented with 10% of horse serum, L-Glutamine, Sodium Pyruvate, Gentamycin and Hypoxanthine, Aminopterin, Thymidine (HAT) mixutre (Beit Haemek Ill.) and were further cultured for additional two weeks in a similar growth medium with Hypoxanthine, Thymidine (HT) mixture in 96F W plates (DeGroot Grainer Germany). Culture supernatants from each well were screened for the presence of anti-MUC1-SP-M IgG antibodies (Abs) by ELISA. Hybridoma cells from wells producing Abs were isolated retested and subjected to sub-cloning. Large-scale Abs production of selected clones was achieved by purifying monoclonal antibodies (mAbs) from culture media using anti-Mouse IgG agarose column (Cat. No A6531, Sigma, Israel). Isotyping of mAbs was performed using the Isostrip kit (Roche Cat. no. 1493027).

Monoclonal Antibody Specificity

Binding experiments performed in mouse No. 1 (M1), as presented in FIG. 1 D, showed strong binding of >1:12,800 titer against the immunizing peptide MUC1-SP-M, moderate binding of >1: 1800-3600 titers to peptides MUC1-SP-S1, MUC1-SP-S2 and MUC1-SP-S3 (denoted by SEQ ID NO.4, 5 and 6, respectively) and low binding >1:800 titer to peptides MUC1-SP-S4 and MUC1-SP-S5 (denoted by SEQ ID NO.7 and 8, respectively). No binding was observed with the MUC1-TRA-L peptide.

Hybridoma formation resulted in 2 monoclonal antibodies, namely SPmAb-2.1, originated from mouse No. 1 and having an Ig-gamma1 isotype, and SPmAb-6, originating from mouse No. 2 and having an Ig-gamma2a isotype. The specificity of the two generated mAbs was validated by performing binding and competition assays as those detailed above (FIG. 1 E) in the presence of the various free soluble peptides indicated therein. As demonstrated in FIG. 1 E, the peptides MUC1-SP-M, MUC1-SP-S1 and MUC1-SP-S2 present about 60%, 50% and 80% inhibition, respectively, with respect to the mAb SPmAb-2.1, while the peptides MUC1-SP-S4 and MUC1-SP-S5 both showed around 30% inhibition with respect to the same mAb. Interestingly, the peptides MUC1-SP-S4 and MUC1-SP-S5, manifested about 80% and 65% inhibition, respectively, of mAb SPmAb-6, while the peptides MUC1-SP-M, MUC1-SP-S1 and MUC1-SP-S2, presented about 63%, 25% and 20% inhibition, respectively, of the same mAb. No inhibition was manifested by the MUC1-TRA-L peptide, for both mAbs. Based on these results the minimal epitope of SPmAb-2.1 is located within the sequence of MUC1-SP-S2 peptide (denoted by SEQ ID NO.5) and the minimal epitope of SPmAb-6 is located within the sequence of MUC1-SP-S4 peptide (denoted by SEQ ID NO.7).

Antibody Screening Assay

Screening of rabbits hyperimmune sera, mice hyperimmune sera and hybridoma producing anti-MUC1-SP-M IgG mAbs was performed using an ELISA protocol, as follows: 96 well ELISA plates (F96 Maxisorp, Nunc, Denmark) were activated for 1 h with 0.1% of Glutaraldehyde (Sigma, Ill.) in carbonate buffer (pH=9). Plates were then coated with 50 µl of the evaluated peptide (as detailed above), at 5 µg/ml, in carbonate buffer, for overnight incubation at 4° C. followed by blocking for 2 h at room temperature with a blocking buffer consisting of PBS supplemented with 5% FBS and 0.04% Tween 20 (ICN Biomedical Inc, USA). Evaluated sera samples from MUC1-SP-M immunized animals were then diluted 1:100 plus 7 additional dilutions in PBS supplemented with 5% FBS and 0.04% Tween 20. Hybridoma growth medium were used (without dilution) and incubated for 2 h at room temperature. Next, 50 µl/well of the secondary anti-mouse or anti-rabbit IgG antibody HRP-conjugate (Jackson ImmunoResearch, USA) was added, at a final dilution of 1:10,000 in a blocking buffer and incubated for 1 h at room temperature. Plates were then developed with TMB/E solution (3,3',5,5-tetramethylbenzidine, CHEMICON, Millipore, USA) according to manufacture instructions.

For peptide antibody competition assays, rabbit or mice hyperimmune sera and Hybridoma growth medium were incubated together with 1 µg/w of different peptides on 96 well ELISA plates (F96 Maxisorp, Nunc, Denmark) activated with Glutaraldehyde as described above. The competition assay was performed as described for the ELISA above.

Example 2

Antibodies Recognize MUC1 SP on the Cell Surface of Preloaded APC

Cell surface expression of an antigen is an important advantage for its use as a target for antibody recognition. Such cell surface expression and antibody recognition can be employed for various diagnostic and therapeutic purposes.

In the following example it is demonstrated that the antibodies of the invention are capable of recognizing MUC1 SP expressed on the surface of preloaded antigen presenting cells (APC).

An anti MUC1 SP polyclonal antibody preparation, SPImAb-3A was used to evaluate the expression of MUC1 SP on the cell surface of cells. This evaluation was performed using Fluorescence-activated cell sorting (FACS) analysis.

SPImAb-3A staining of naïve macrophages (expressing both MHC class I and II molecules), which were preloaded with the VXL100 peptide or a control peptide (such as VXL101 and VXL102 which are the SP domains of non-MUC1 TAA ARMET and BAGE, respectfully) was analyzed using FACS. 100 µl containing cells at a concentration of $10 \times 10^7$ cells/ml were incubated for 30 min at RT in FACS staining buffer, consisting of PBS supplemented with 3% FCS, 0.1% sodium azide, and 10% Human AB serum (Sigma Israel, Rehovot, Israel). Then, the cells were transferred into FACS tubes (BD Falcon™, Franklin Lakes N.J. USA) and the staining buffer was carefully removed. For the staining step, 30 µl of FITC-conjugated (Sigma Israel, Rchovot, Israel) H23, or SPImAb-3A in staining buffer (without AB serum) were added for an incubation of 30 min at RT, in the dark. Following this incubation step, cells were washed with 3 ml of staining buffer, and re-suspended in 0.5 nil PBS. Samples were then analyzed in a LSR II FACS (BD Biosciences, San Jose, Calif., USA). The same macrophages, unloaded, or the anti-MUC1 TRA, or mAb H23 antibodies were used as controls.

H23 is monoclonal antibody that was raised against the human breast cancer cell line T47D and recognizes the epitope APDTRP on the non-glycosylated form of MUC1's TRA (Keydar et al Proc. Natl. Acad. Sci. USA 1989, 86:1362-1366). MAb H23 recognizes the soluble MUC1's TRA domain in sera or on cancer cells. It also recognizes the 25mer peptide VXL25.

The Results, demonstrated in Table 2 below, revealed 30% specific binding by SPImAb-3A antibodies to VXL100-loaded macrophages, compared to no binding of SPImAb-3A antibodies to unloaded naïve macrophages or to macrophages loaded with control peptides (VXL101, VXL102). The absence of binding to un-loaded macrophages suggests that SPImAb-3A antibodies specifically recognize the MUC1 epitope, which is not presented on naive primary macrophages.

TABLE 2

| Cells | | Expression (%) | |
|---|---|---|---|
| Naïve Macrophage | Species | H23 | SPImAb-3A |
| Unloaded | Human | 13% | 0 |
| Loaded with VXL100 | Human | 12% | 30% |
| Loaded with VXL101 | Human | 44% | 0 |
| Loaded with VXL102 | Human | 26% | 4.8% |

In addition, the results presented in Table 2 demonstrate a higher non-specific binding observed for H23 antibodies (at the range of 10-40%), suggesting this antibody is of a lower specificity for the assayed peptides. The high specific binding demonstrated for SPImAb-3A antibodies, particularly in view of the fact that SPImAb-3A is a polyclonal antibody, wherein H23 is a monoclonal antibody, is fundamental in confirming that SPImAb-3A has both a high MUC1 specific recognition and a lower background binding properties to naïve macrophages, in comparison to H23.

Example 3

Anti-MUC1 SP Antibodies Bind to MUC1-positive Tumor Cells

In the following example it is demonstrated that the antibodies of the invention are capable of recognizing cell surface expressed MUC1 SP on various types of cells.

An enriched IgG fraction of the rabbit R23 hyper immune sera (polyclonal) R23IgG, the IgG purified monoclonal antibodies SPmAb-2.1 and SPmAb-6 and the H23 antibodies were used to determine the expression profile of MUC1 SP and other MUC1 epitopes on various human tumor cells (primary cells and cell lines). Binding of the antibodies to the epitopes was measured using FACS analysis and the results are presented as percent or geometric mean of positive binding to cells, related to the species-specific Isotype control. The FACS analysis was performed as described above.

Figure 2A:
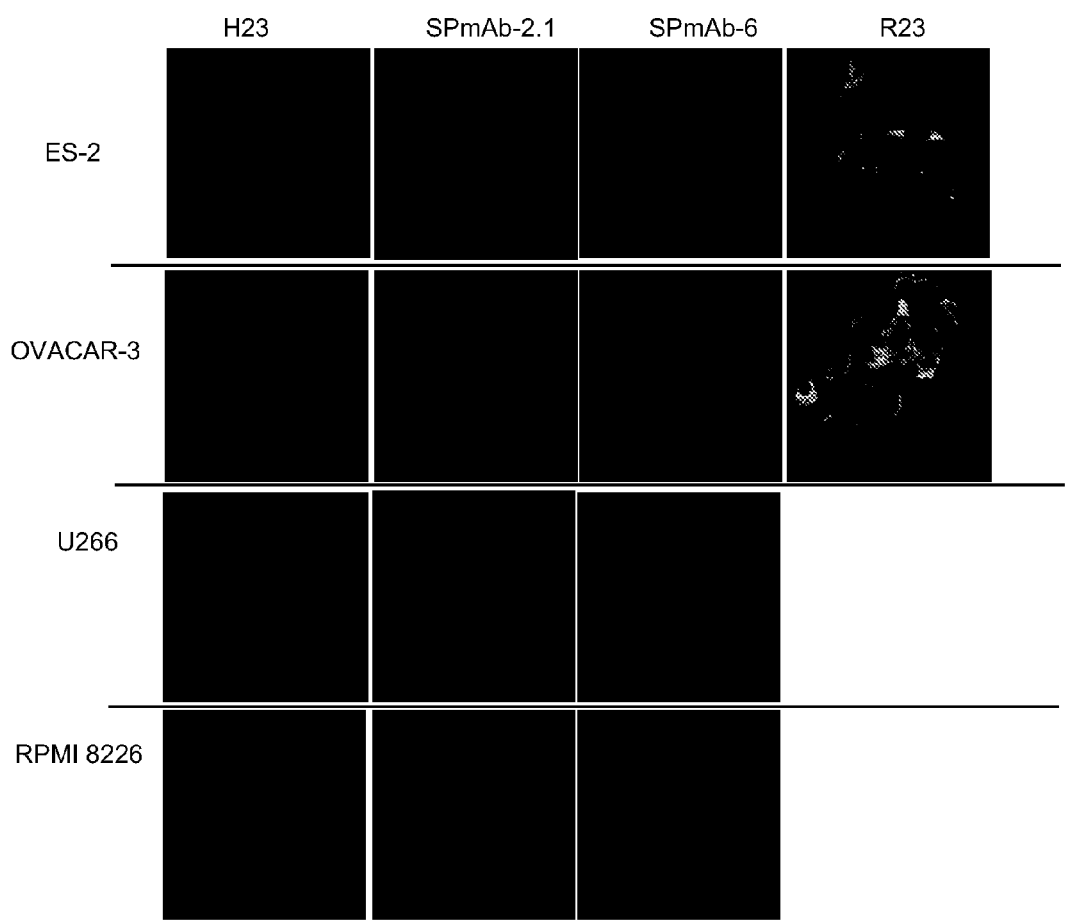
FIG. 2A shows photographs of immunofluorescence microscopy staining of various cancer cell types both solid and non-solid (ES-2, OVACAR-3, U266 and RPMI 8226) different MUC1 SP antibodies: the control MUC1 TRA monoclonal antibody H23, monoclonal antibodies (mAbs) SPmAb-2.1 and SPmAb-6 and the IgG fraction of the hyper immune polyclonal antibodies R23.
Figure 2B:
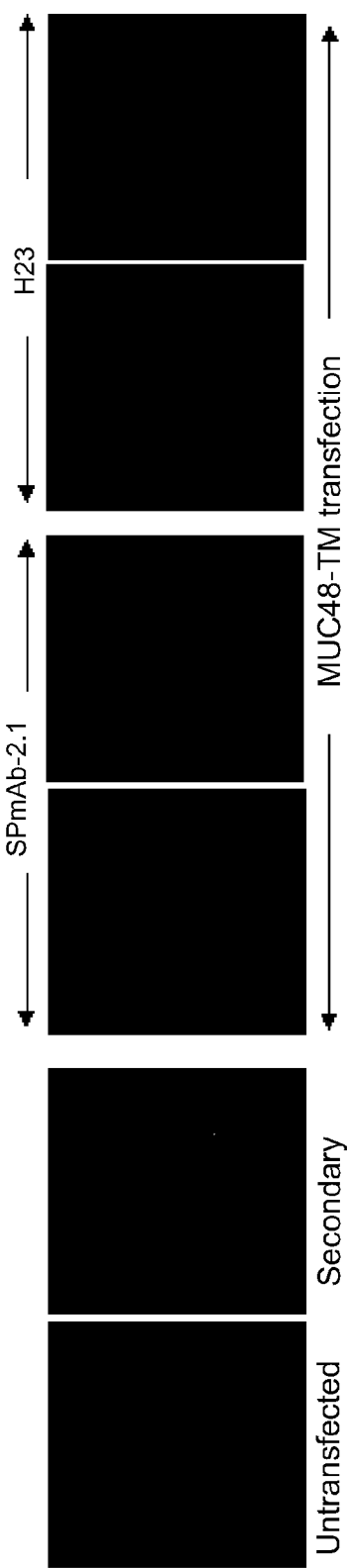
FIG. 2B shows photographs of immunofluorescence microscopy staining of ES-2 MUC1 negative ovarian cells (untransfected or transfected with a MUC-TM construct containing both alfa and beta sub-units) with the anti-MUC1 SP monoclonal antibody (mAb) SPmAb-2.1 and the MUC1 TRA mAb H23.

Flow cytometric analysis demonstrated that SPmAb-2.1, SPmAb-6 and R23IgG have respectively moderate to high binding to MUC1 expressing tumor cells, both in solid tumors e.g. OVCAR-3 Ovarian carcinoma tumor, and in non-solid cancer cells e.g. RPMI, U266 MM cells, Raji and Ramos B-Lymphocytic Leukemia tumors and ARH77 plasma cell Leukemia (Table 3). The monoclonal antibody directed against MUC1 TRA, namely, H23 [Keydar I, et al. PNAS USA 86:1362-1366 (1989)] was used as a to positive control for MUC1 alfa-subunit (the part of MUC1 containing the TRA domain which is cleaved and released to the serum) and showed reactivity with similar binding strength to the IgG fraction of the R23 antibodies. In contrast, MUC1 negative melanoma cell-lines SK-mel-28, SK-mel-1 and MUC1-negative ovarian cell-line ES-2 were consistently negative with all antibodies (Table 3) supporting the selective binding to MUC1. The nature and location of the antigen recognized by the different MUC1 SP antibodies vs. the control MUC1 TRA antibody H23, was further characterized by Immunofluorescence microscopy staining. No staining of ES-2 ovarian carcinoma cells was seen with mAb H23, IgG fraction of the polyclonal antibodies R23 and mAbs SPmAb-2.1 and SPmAb-6 (FIG. 2A). However, membrane staining of OVACAR-3 ovarian carcinoma as well as MM RPMI 8226 and U266 cell-lines was achieved with each of the antibodies (FIG. 2A). These findings were further validated by showing the ability of anti-MUC1 SP mAb SPmAb-2.1 and the MUC1 TRA mAb H23 to specifically stain ES-2 MUC1 negative ovarian cells following transfection with the MUC1-TM construct (FIG. 2B). The MUC1-TM construct contains the entire MUC1 i.e. the alfa plus beta subunits and hence it includes the TRA and the SP domains in case that it is not chopped by signal peptidase in the ER. In summary, these results confirmed MUC1-associated membrane binding to each of the MUC1's SP antibodies as observed in the flow cytometry experiments.

TABLE 3

| Human Cell-lines | Origin | Mouse control | H23 | SPmAb-6 | SPmAb-2.1 | Rabbit control | R23 |
|---|---|---|---|---|---|---|---|
| ES-2 | Ovarian Carcinoma | 234 | 32 | 248 | 237 | 251 | 247 |
| OVCAR-3 | Ovarian Carcinoma | 370 | 456 | 11440 | 1019 | 418 | 10800 |

TABLE 3-continued

| Human Cell-lines | Origin | Mouse control | H23 | SPmAb-6 | SPmAb-2.1 | Rabbit control | R23 |
|---|---|---|---|---|---|---|---|
| MCF7 | Breast Carcinoma | 230 | 004 | 1091 | 413 | 236 | 4705 |
| MDA-453 | Breast Carcinoma | 182 | 80 | 559 | 290 | 165 | 2443 |
| MDA-231 | Breast Carcinoma | 245 | 66 | 591 | 312 | 215 | 1931 |
| Raji | B-Lymphoblastic Leukemia | 131 | 03 | 307 | 179 | 128 | 519 |
| Ramos | B-Lymphocytic Leukemia | 198 | | 660 | 402 | 111 | 384 |
| U266 | Multiple Myeloma | 485 | 039 | 661 | 574 | 471 | 1716 |
| RPMI822S | Multiple Myeloma | 745 | 585 | 1190 | 1154 | 738 | 2331 |
| ARH-77 | Plasma cell Leukemia | 176 | 68 | 691 | 439 | 161 | 3966 |
| SK-mel-28 | Melanoma | 117 | 19 | 114 | 112 | 113 | 117 |
| SK-mel-1 | Melanoma-Metastasis | 352 | 25 | 342 | 345 | 350 | 348 |

The human B-Lymphocytic leukemia lines Raji and Ramos, the human MM cell lines U266, and RPMI 8226 and the human Plasma cell Leukemia line ARH-77 were grown in suspension in RPMI-1640 medium supplemented with 10% FBS, L-Glutamine, Sodium Pyruvate, non-essential amino-acids, HEPES and Gentamycin (Biological Industries, Israel). The human ovarian carcinoma line OVARCAR-3 was grown as adherent monolayer culture in RPMI-1640 medium supplemented with 15% to FBS, L-Glutamine, Sodium Pyruvate and Gentamycine. The human ovarian carcinoma line ES-2 and melanoma lines SK-mel-28 were grown as adherent monolayer cultures and the human Melanoma line SK-mel-1 was grown as suspension culture in DMEM medium, supplemented with 10% FBS L-Glutamine, Sodium Pyruvate and Gentamycine. All cell lines were purchased from the American Type Culture Collection (ATCC, Manassas, USA). As a positive control for MUC1 expression, the anti-MUC1 TRA mAb II23 was used. This monoclonal antibody was raised against the human breast cancer cell line T47D 16 and recognizes the epitope APDTRP on the non-glycosylated form of MUC1. As a negative control in FACS analysis, mice anti goat or rabbit ant-mouse IgG-FITC conjugated were used (Jackson immunoResearch, USA).

Flow cytometry for cell lines was performed as follow: $1 \times 10^7$ evaluated cells were washed once with PBS and incubated for 30 min in staining buffer consisting of PBS supplemented with 3% EBS, 10% Hu AB sera (i.e. pooled human sera obtained from donors) and 0.1% sodium azid in FACS tubes, over-night. Next, buffer was removed by centrifugation and 50 µg/sample of FITC conjugated Abs were added to different tubes for 30 min at R.T. Labeled cells were washed twice, fixed in BD CellFIX (Becton Dickenson, USA) according to the manufacturer's protocol and stored at 4° C. until analyzed. Four-color flow cytometry analysis was performed on the LSR II (Becton Dickenson Immunocytometry Systems, USA) and the data were analyzed using FlowJo software (TreeStar, USA).

Conjugation of antibodies with FITC was performed as followed: 50 µl of FITC (1 mg/ml solution. Sigma, Ill.) diluted in DMSO (Sigma, Ill.) were added to 0.5 ml of IgG (2 mg/ml) diluted in 0.1M sodium bicarbonate buffer at pH=9 and incubated, with stirring, for 8 h at 4° C. At the end of this incubation step, the FITC-1gG conjugation was to dialyzed against PBS for 48 h at 4° C.

Example 4

Figure 3A:
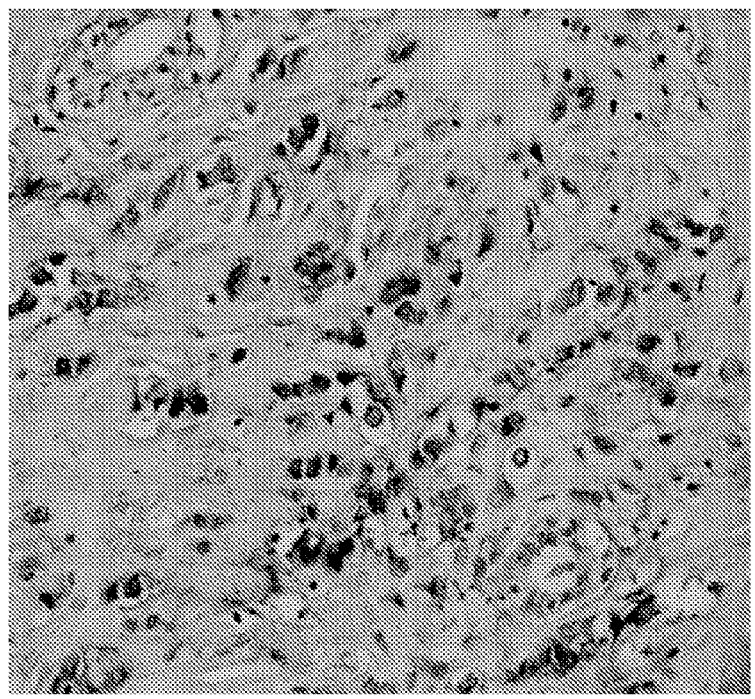
FIG. 3 shows photographs of specific staining of tumor tissue obtained from breast cancer patient with H23 (FIG. 3A) and SPmAb-2.1 (FIG. 3B).
Figure 3B:
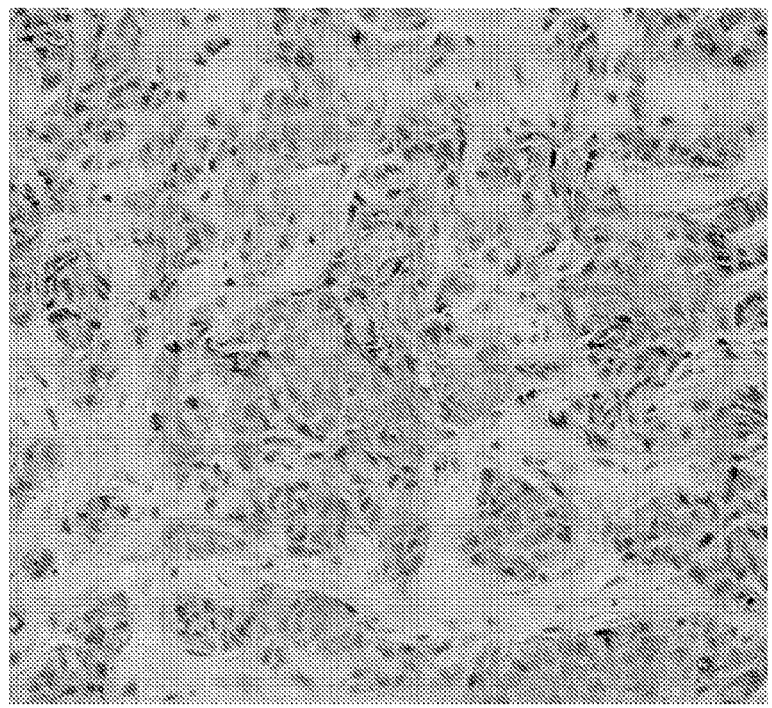

Expression of MUC1 SP and MUC1 on Solid Tumors as Assayed by Immunohistochemistry The ability of anti-MUC1-SP antibodies to diagnose solid tumors was evaluated by immunohistochemistry analysis of breast cancer tissue in paraffin blocks (prepared by the Pathology Department at Haddasah University Hospital, Jerusalem). The Results, presented in FIG. 3 are an example of the positive staining observed in sections taken from an infiltrating duct carcinoma of the breast and demonstrate specific staining of tumor tissue obtained from breast cancer patient with H23 (FIG. 3A) and SPmAb-2.1 (FIG. 3B). As can be seen, the number of stained cells per tumor section varied as well as the intensity of staining per cell, thereby confirming specificity.

Immunohistochemistry analysis was performed on de-paraffinized tissue slices using H23 or SPmAb-2.1 MUC1 antibodies at a final concentration of 50 µg/ml for 1 h at room temperature. PolyScan HRP/DAB detection system kit (Cell Marque, USA) was then used according to the recommended protocol.

Example 5

Expression of MUC1 SP and MUC1 on BM Cells of MM Patients

Evaluating the expression levels of SP epitopes present on tumor cells obtained from a patient is a valuable tool in selecting subjects that may benefit from treatment with a vaccine comprising MUC1 SP, such as ImMucin [Kovjazin, R. et al. Vaccine (2011)]. The vaccine comprises an SP domain of a protein and was shown to raise a powerful specific immune response against said SP domain.

In the following example it is demonstrated that the antibodies of the invention are capable of binding to cell surface expressed MUC1 SP on bone marrow cells of patients suffering from multiple myeloma (MM).

The ability of R23IgG polyclonal antibodies to selectively bind tumor cells was investigated in an ex-vivo setting with malignant plasma cells found in bone marrow aspirates obtained from three patients with multiple myeloma (MM). The heterogeneous cell population in the aspirates allows direct assessment of MUC1-specific SP (using to the R23IgG antibody) and MUC1-TRA (using the H23 antibody). These antibodies are expected to bind MM cells that express MUC1, while minimally binding to non-MUC1 expressing cells that are present in the same aspirate samples.

The binding properties of R23IgG and H23 antibodies, in terms of intensity (per sample) and frequency (%) were compared among different MM patients, using FACS analysis. Bone marrow aspirates (2-3 ml) were drawn from 3 patients (50-75 years) with slowly progressing asymptomatic MM.

FACS analysis of BM cells was performed as follows: 1 ml of BM cells obtained from a patient was incubated in 15 ml polypropylene tubes (CellStar, Greiner, Fricknhausen, Germany), for 15 min at RT, in the presence of 2 mM EDTA. Then, 10 ml (10-fold diluted in Double Distilled Water) of BD FACS lysing Solution (Catalog #349202, 10×) was added to the cells, for further incubation of 10 min (RT). Next, the remaining cells were washed with staining buffer, using a centrifugation step of 5 min at 1500 RPM, and placed in FACS tubes (BD Falcon™, Franklin Lakes N.J. USA). Cells were then blocked for 15 min with staining buffer, supplemented with 10% AB serum (Sigma Israel, Rehovot, Israel). Staining was performed using APC-conjugated antibodies CD138 (IQP, Groningen, Netherlands), eFluor450-Kappa, PE-Lambda (ebiosciences, San-Diego, Calif., USA) and FITC-conjugated (Sigma Israel, Rehovot, Israel) H23, R23IgG, which were added for an incubation step of 30 min, at RT, in the dark. Following this step, cells were washed with 2 ml of staining buffer and re-suspended in 0.5 ml PBS. Samples were then analyzed using a LSR II FACS (BD Biosciences, San Jose, Calif., USA).

Figure 4A:
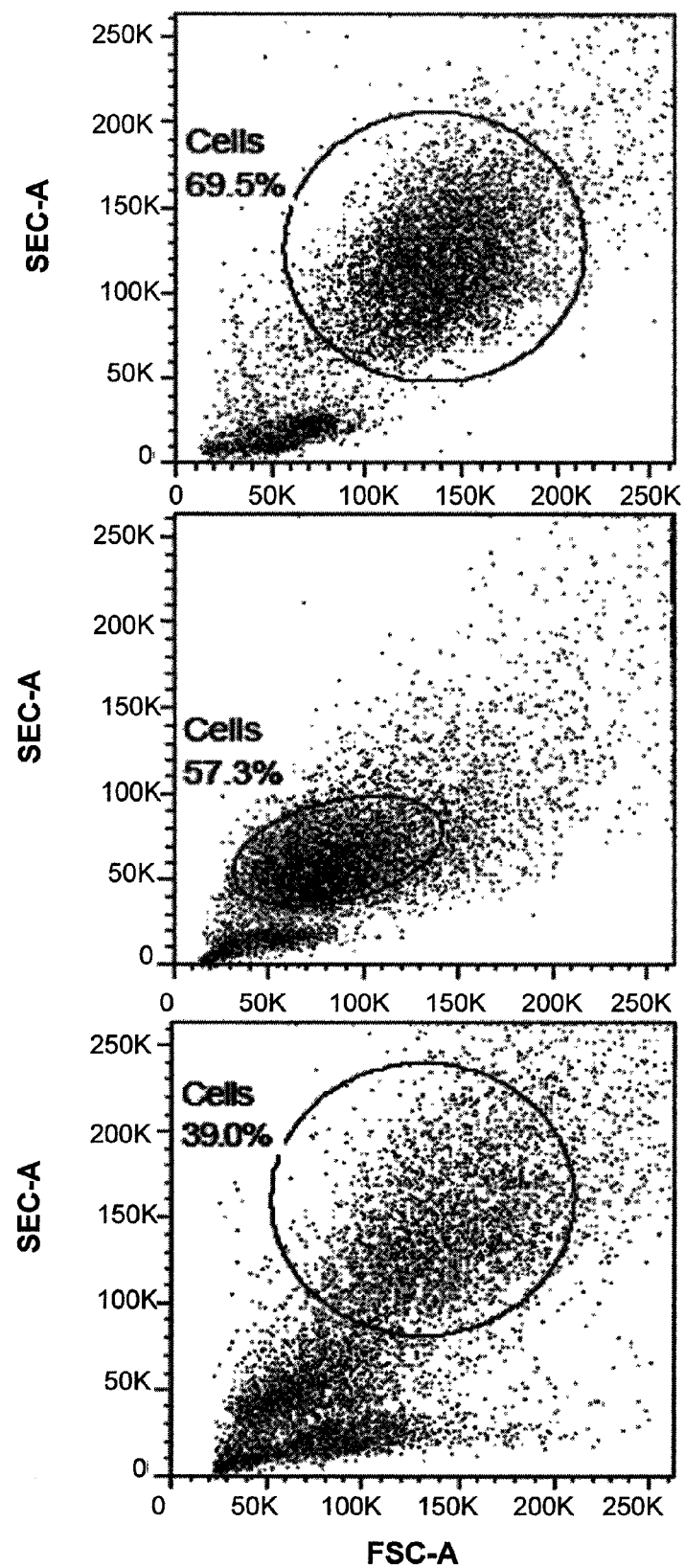
FIG. 4A-4E shows graphical representations of FACS analysis data.
Figures 4B, 4C:
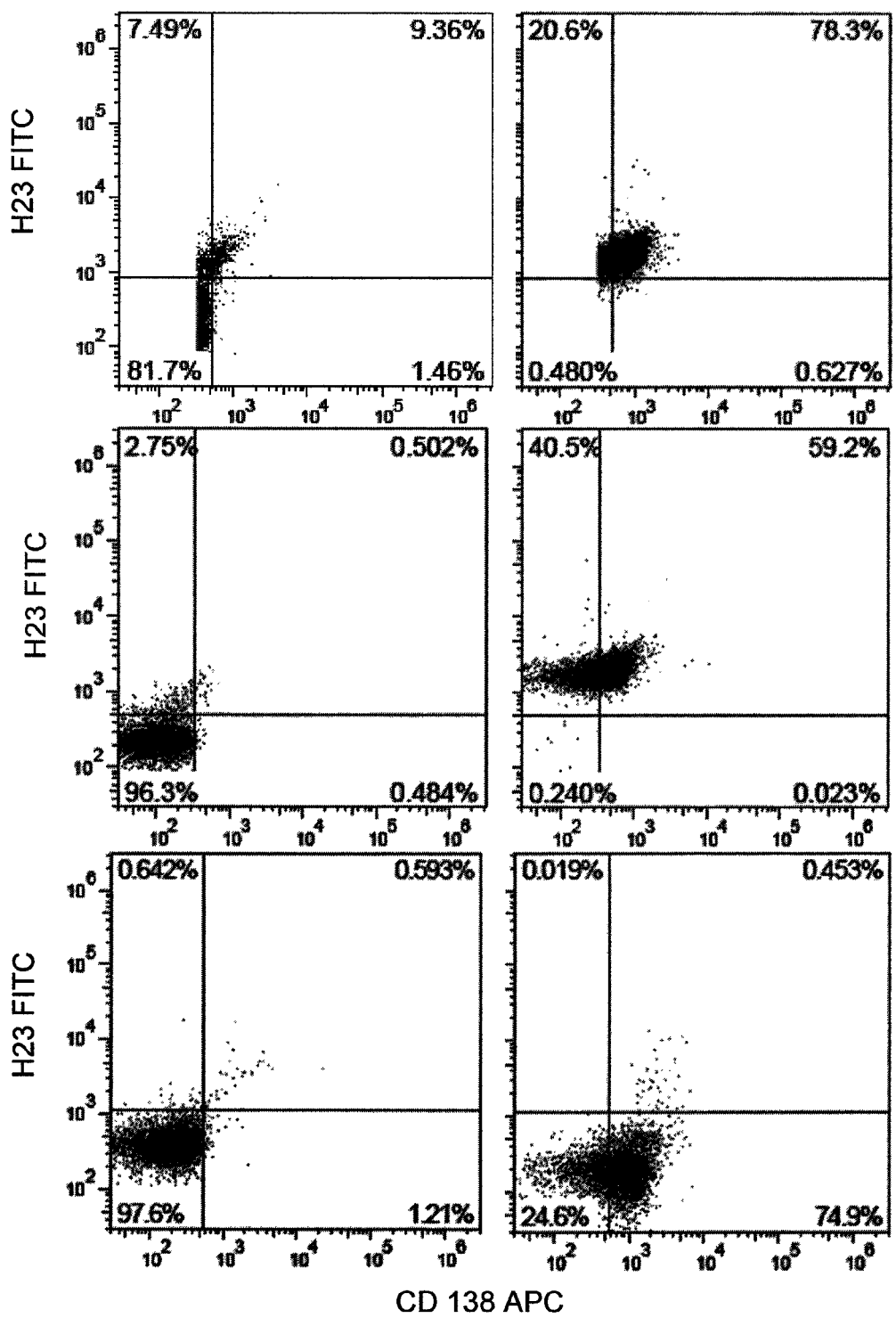
Figures 4D, 4E:
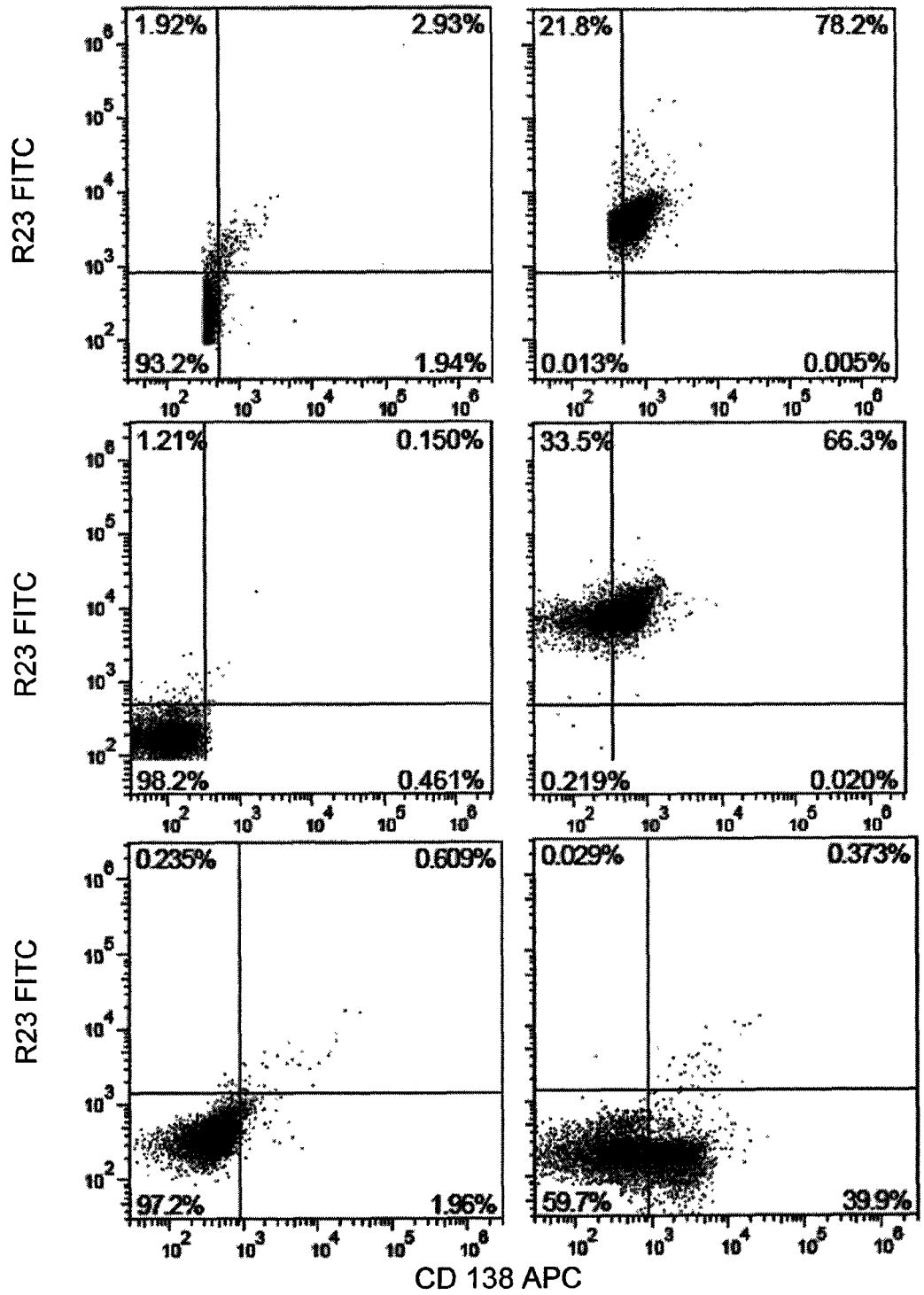

A population of "large cells" was initially gated by side vs. forward scatter (FIG. 4A) their phenotype as plasma cells was verified by staining with anti-Kappa light chain-eFluor 450 and anti-Lambda-PE labeled antibodies, as detailed below. This gated cells population was next analyzed for MUC1 TRA (FIG. 4C) and MUC1 SP (FIG. 4E) expression on CD138 positive MM cells. Anti-CD138-APC labeled antibody was used for this analysis, to further select MM cells, and the R23IgG and H23 antibodies were labeled with FITC fluorophores. In each experiment species matched control antibodies were used for MUC1 staining, either normal mouse IgG-FITC conjugated (FIG. 4B), or normal rabbit IgG-FITC conjugated (FIG. 4D).

The results with freshly obtained bone marrow aspirates from 2 MM patients (P#1 and P#II) revealed R23IgG immunoreactivity in 78.2% and 66.3% of the two CD138 positive cell populations (FIG. 4, column E) and H23 immunoreactivity in 78.3% and 59.2% of the two CD138 positive cell populations (FIG. 4, column C). The specificity of the staining was high, with marginal staining for both CD138 positive/MUC1 negative cells and to species matched control antibodies.

In contrast, the expression levels of MUC1 TRA and SP (based on the results obtained with H23 and R23IgG, respectively) were low in the third aspirate (P#3), 0.37%, and 0.45% respectively, while CD138 expression levels in this aspirate was still moderate (74.9% and 39.9%). In these three patients, the R23IgG and H23 antibodies seem to recognize MUC1 SP and MUC1 TRA (respectively) in the same population of malignant plasma cell although the staining intensity with R23IgG vs. H23 was up to one log higher.

The analysis in this study was part of a screening process performed for enrolment into a phase VII clinical trial of the cancer vaccine ImMucin (protocol VAXIL-001). The study was approved by the Ethics Committee of Haddasah University hospital, Jerusalem, Israel and the Israeli Ministry of health.

Importantly, the results obtained with R23IgG provide a tool for selecting patients which may benefit from treatment with an agent directed against the MUC1 SP epitope, in particular, with a therapeutic vaccine comprising the MUC1 SP (e.g. ImMucin). In addition, another plausible therapeutic approach would be to target MUC1 SP positive cancer cells using anti-MUC1 SP antibodies optionally conjugated to anti cancer agents.

Example 6

Figure 5A:
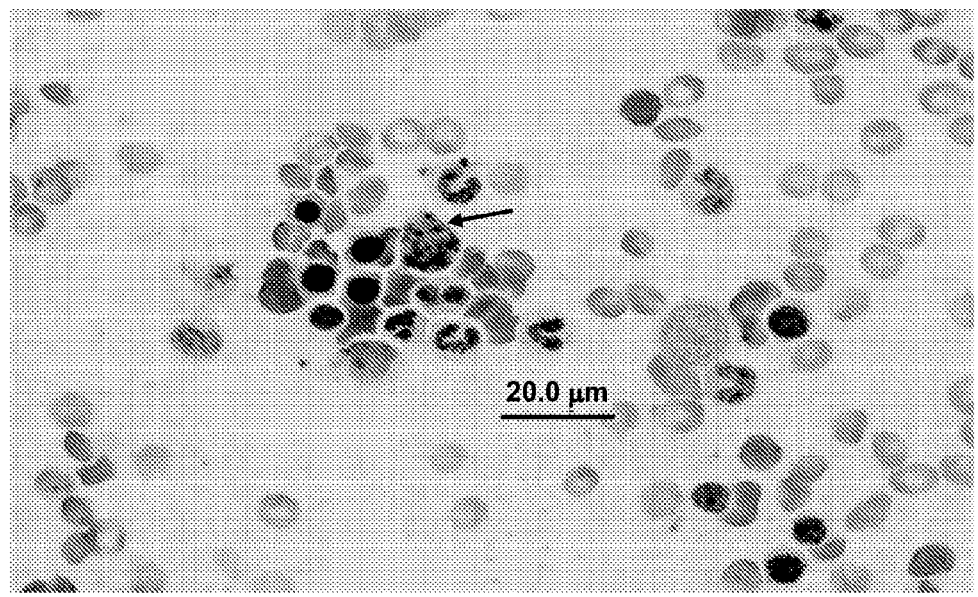
FIG. 5 shows photographs of plasma cells obtained from bone marrow aspirates of MM patients stained with II23 (FIG. 5A) or R23IgG (FIG. 5B). Stained cells are indicated by an arrow.
Figure 5B:
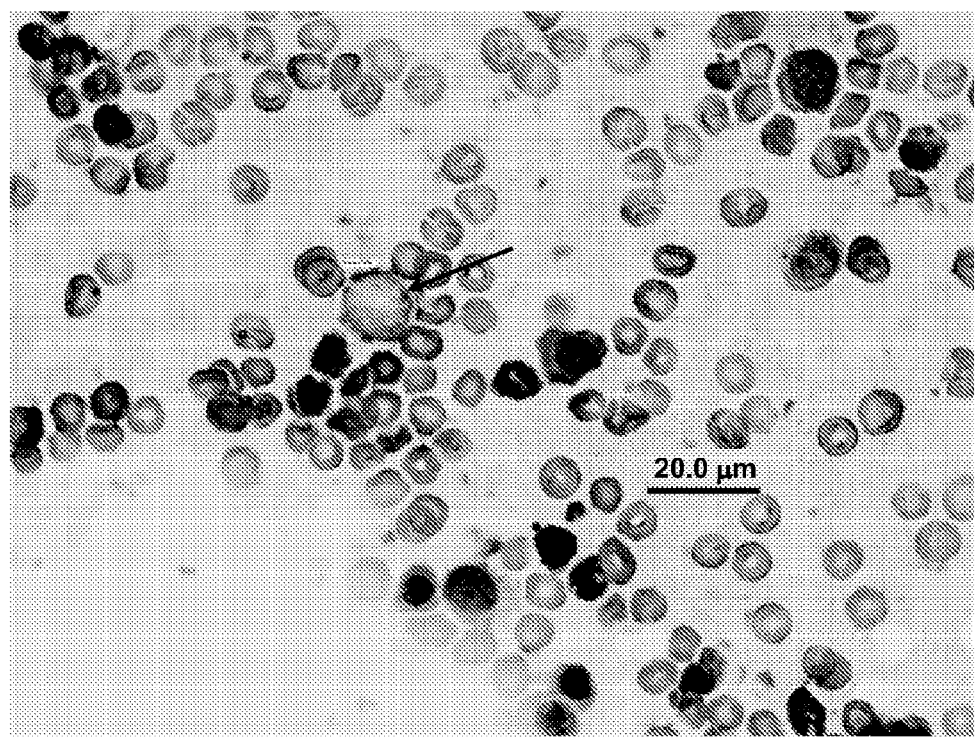

Expression of MUC1 SP and MUC1 on BM of MM Patients as Assayed by Immunohistochemistry The specificity of R23IgG as compared with H23 antibodies was further confirmed using Immunohistochemistry, by staining fresh samples prepared from BM aspirates of MM patients. As shown in FIG. 5, specific binding of both antibodies to plasma cells was observed (the positive stained cells are indicated by an arrow). However, while II23 (FIG. 5A) manifested strong binding, which was mainly localized inside the cells, staining with R23IgG (FIG. 5B) was more delicate and was mainly localized on the cell membranes. The results obtained in the immunochemistry to analysis were consistent with the results obtained in the FACS analysis of the BM cells, which were obtained for the same patients and thus reconfirmed their specificity.

Immunohistochemistry analysis was performed as follows: BM samples derived from patients were placed on slides, air-dried and fixed for 10 min at −20° C., with acetone. Staining with H23 and R23IgG antibodies was performed according to the protocol of the HRP/DAB Detection System Cat# CMQ 951D (Cell Marque, USA) with additional staining with Giemsa solution (MERCK HX888942) at the final step.

In summary, binding was demonstrated for both types of antibodies those directed against the MUC1 SP and those directed to the non-SP epitope TRA, in solid and in non-solid MUC1 positive tumor cells, reconfirming the ability of anti MUC1 SP antibodies to detect MUC1 presentation on the cell surface of cells. Furthermore, binding of R23IgG was found to be stronger and more specific than the binding of H23 (which is directed to a non-SP portion of MUC1), particularly in the case of MM/B-cell lines.

Example 7

Evaluation of Anti-MUC1 SP Antibodies in a Complement Dependent Cytotoxicity (CDC) Assay In the following example, the functional ability of the antibodies of the invention to recognize and affect tumor cells bearing the antigen was tested by means of tumor specific lysis.

Figure 6A:
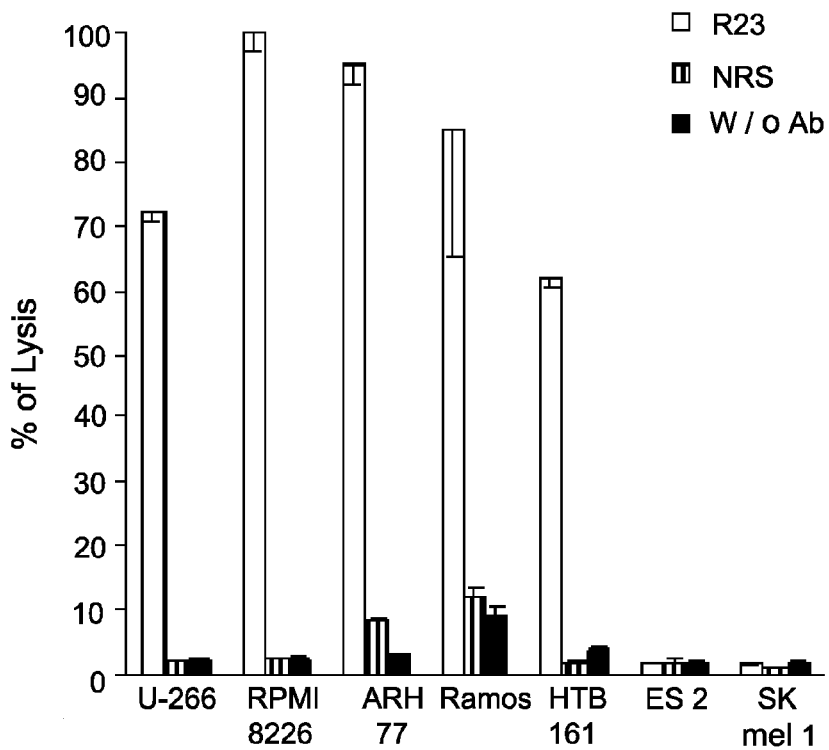
FIGS. 6A and 6B is a graphical representation of the percent of cell lysis in a Complement dependent cytotoxicity (CDC) assay using the rabbit polyclonal antibodies R23IgG (FIG. 6A) and the two monoclonal antibodies, SPmAb-2.1 and SPmAb-6 (FIG. 6B) on various target cell lines.

Complement dependent cytotoxicity (CDC) analysis using the rabbit polyclonal antibodies R23IgG (FIG. 6A) and the two monoclonal antibodies, namely, SPmAb-2.1 and SPmAb-6 (FIG. 6B) demonstrated a strong lysis of MUC1 expressing cells. As demonstrated in FIG. 6A, R23IgG polyclonal antibodies manifested 60-100% lysis of solid tumors OVACAR-3 ovarian cells, and of the non-solid tumors, U266, RPMI 8226, MM, ARH-77 and Ramos Leukemia tumor cells.

Figure 6B:
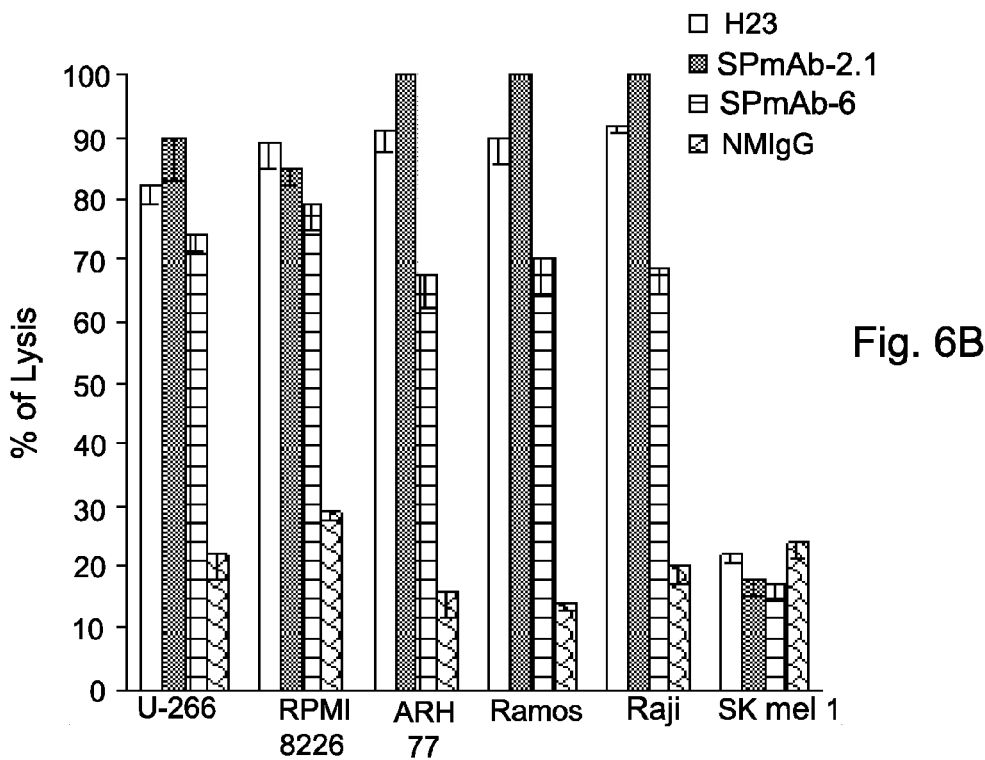

In a similar manner, as demonstrated in FIG. 6B, SPmAb-2.1 and SPmAb-6 manifested strong specific lysis of >90% and 60-70%, respectively of the same cell lines. In these experiments H23 demonstrated a similar trend of 80-90% lysis compared to SPmAb-2.1 and SPmAb-6 (FIG. 6B). The lysis by each of the anti-MUC1 antibodies was highly statistically significant ($p > 0.001$ or more, t-test), with respect to to the MUC1 expressing cell lines vs. MUC1-negative ovarian cell line ES-2 and melanoma cell line SK-mel-1. Moreover, the negative control, such as normal mouse sera (NMS), Normal mouse IgG (NM IgG) and normal rabbit sera (NRS) all manifested significantly lower percentage of lysis (see FIGS. 6A and 6B). Generally, the CDC lysis efficacy positively correlates with the MUC1 cell surface expression levels evaluated by flow cytometry analysis (Table 3). One exception from this observation was found with mAb SPmAb-6, which demonstrated high cell surface binding and lower CDC. The potential explanation for this difference can be related to its Ig-gamma2a isotype which was previously shown to be less active than Ig-gamma1 in CDC [Watier, H. et al., Transplantation 62(1): 105-113 (1996) and Chuntharapai, A. et al., J. Immunol., 166(8):4891-4898 (2001)].

CDC analysis was performed as described above, with the following changes: Cells were incubated with the antibodies H23, R23IgG, SPmAb-6 or SPmAb-2.1 (100, 50 and 10 μg/ml). Plates (96-well) were from Griner (De Groot, Germany) and a PerkinElmer Beta-counter was used for evaluation (IL USA). In addition, normal mice or rabbit IgG antibodies were used (Chemicon, Millipore, USA). The results were statistically analyzed with student's t-test. In all tests, the minimum level of significance for a 2-tailed test was set at P<0.01.

Example 8

Sera Expression Levels of sMUC1 in Healthy Donors and Cancer Patients

Expression levels of soluble MUC1 (sMUC1, MUC1 Ag, or sMUC1 TRA) in sera samples, obtained from healthy donors and cancer patients, were determined using the commercial M4H2 anti-TRA monoclonal antibody, which recognizes the core antigen of soluble MUC1.

Levels of sMUC1 were evaluated using ELISA. Briefly, the ELISA protocol included ELISA plates (F96 Maxisorp, Nunc, Roskild, Denmark), a commercial anti-MUC1 monoclonal antibody that was raised against a TRA peptide and recognizes soluble MUC1's core antigen (clone M4H2), and an ELISA kit (HyTest, Turku, Finland), which was used according to the manufacturer's protocol. sMUC1 levels were evaluated using seven serial 100 μl dilutions of patient's sera, starting at a 1:5 dilution. As a MUC1 positive control, six dilutions (starting at a 1:5 dilution) of supernatant collected from the DA-3TM cell line were used. The ELISA plates were developed with TMB/E solution (CHEMICON, Millipore, Billerica, Mass., USA). The reactions were terminated by the addition of 50 μl/well of 10% sulfuric acid. The results were measured at 450 nm. In cases where a pure antigen or specific antibody was not used as standards, this assay consisted of measuring the "Specific titer" rather than the absolute concentration.

The Tables below summarize the results obtained for naïve healthy donors (Table 4), cancer patients with solid tumors (Table 5), each of which having a different disease stage and a different tumor indication (mainly Colon and Rectal cancers), and multiple myeloma patients (Table 6) with various stages of MM.

TABLE 4 sMUC1 and anti-MUC1 autoantibodies levels in naïve donors

| Sample No. | Sample characterization | sMUC1 TRA (ug/ml)[1] | sMUC1 SP (ug/ml)[1] | Anti-MUC1 TRA Ab (μg/ml)[2] | Anti-MUC1 SP Ab (μg/ml)[2] |
|---|---|---|---|---|---|
| 1 | Naïve healthy donor | Negative | Negative | 224 | 178 |
| 2 | Naïve healthy donor | Negative | Negative | 265 | 159 |
| 3 | Naïve healthy donor | Negative | Negative | 184 | 145 |
| 4 | Naïve healthy donor | Negative | Negative | 161 | 185 |
| 5 | Naïve healthy donor | Negative | Negative | 205 | 185 |
| 6 | Naïve healthy donor | Negative | Negative | 230 | 200 |
| 7 | Naïve healthy donor | Negative | Negative | 281 | 216 |
| 8 | Naïve healthy donor | Negative | Negative | 318 | 10 |
| 9 | Naïve healthy donor | Negative | Negative | 105 | 110 |
| 10 | Naïve healthy donor | Negative | Negative | 320 | 166 |
| 11 | Naïve healthy donor | Negative | Negative | 203 | 10 |
| 12 | Naïve healthy donor | Negative | Negative | 147 | 200 |
| 13 | Naïve healthy donor | Negative | Negative | 200 | 184 |
| 14 | Naïve healthy donor | Negative | Negative | 134 | 100 |
| 15 | Naïve healthy donor | Negative | Negative | 152 | 10 |
| Average | | | | 208.60 | 137.20 |
| Standard deviation | | | | 65.35 | 72.97 |

1. Sera levels of MUC1 antigen and anti-MUC1 antibodies were measured by ELISA assay as described above. Positive sMUC1 level is set for titer of X > 1:5.

2. Naïve sera for anti-MUC1 TRA antibodies epitope is X ≤ 274 μg/ml and for anti-MUC1 SP autoantibodies is X ≤ 210.2 μg/ml, based on the average plus standard deviation values determined in 15 naïve healthy individuals.

TABLE 5

| Patient | Indication | MUC1 Ag (titer) | Anti-VXL25 Ab (μg/ml) | Anti-VXL100 Ab (μg/ml) | Anti-VXL3A Ab (μg/ml) | Anti-VXL211 Ab (titer) |
|---|---|---|---|---|---|---|
| B#1 | Colorectal | 0 | 294 | 1481 | 333 | >1:100 |
| B#2 | Colon | 1:20 | 382 | 1781 | 708 | >1:100 |
| B#3 | Colorectal | 1:20 | 266 | 2016 | 520 | >1:100 |
| B#4 | Colorectal | 1:5 | 260 | 3744 | 625 | >1:100 |
| B#6 | Lung | 1:5 | 816 | 3136 | 1041 | >1:100 |
| B#7 | Colon | 0 | 47 | 113 | 238 | >1:100 |
| B#9 | Chorionic | 1:40 | 267 | 465 | 362 | >1:100 |
| B#10 | Prostate | 0 | 290 | 460 | 375 | >1:100 |
| B#12 | Colon | | 375.33 | 1523.67 | 516.89 | |
| Average STDEV | | | 249.46 | 1279.43 | 245.74 | |

TABLE 6 sMUC1 and anti-MUC1 autoantibodies levels in multiple myeloma patients

| Patient No. | Patient status | sMUC1 TRA (titer)[1] | sMUC1 SP (titer) | Anti-MUC1 TRA Ab (ug/ml)[2] | Anti-MUC1 SP Ab (ug/ml)[2] | Anti-MUC1 TRA Ab (% Pos.) | Anti-MUC1 SP Ab (% Pos.) |
|---|---|---|---|---|---|---|---|
| 1 | Active disease; under therapy | Negative | Negative | 440 | 740 | + | + |
| 2 | Progressive disease; under therapy | Negative | Negative | 183 | 150 | − | − |
| 3 | At best response; off therapy | 1:10 | Negative | 382 | 312 | + | + |
| 4 | Active disease; under therapy | 1:5 | Negative | 190 | 350 | − | + |

TABLE 6-continued sMUC1 and anti-MUC1 autoantibodies levels in multiple myeloma patients

| Patient No. | Patient status | sMUC1 TRA (titer)[1] | sMUC1 SP (titer) | Anti-MUC1 TRA Ab (ug/ml)[2] | Anti-MUC1 SP Ab (ug/ml)[2] | Anti-MUC1 TRA Ab (% Pos.) | Anti-MUC1 SP Ab (% Pos.) |
|---|---|---|---|---|---|---|---|
| 5 | Active disease; under therapy | 1:10 | Negative | 85 | 50 | − | − |
| 6 | Active disease; under therapy | Negative | Negative | 97 | 130 | − | − |
| 7 | At best response; off therapy | 1:10 | Negative | 355 | 456 | + | + |
| 8 | At best response; off therapy | Negative | Negative | 211 | 581 | − | + |
| 9 | Active disease; under therapy | Negative | Negative | 132 | 1036 | − | + |
| 10 | At best response; off therapy | Negative | Negative | 158 | 746 | − | + |
| 11 | Progressive disease; under therapy | Negative | Negative | 238 | 525 | − | + |
| 12 | Progressive disease; under therapy | Negative | Negative | 63 | 500 | − | + |
| 13 | At best response; off therapy | Negative | Negative | 500 | 1000 | + | + |
| 14 | Active disease; under therapy | 1:10 | Negative | 292 | 884 | + | + |
| 15 | Progressive disease; under therapy | 1:40 | Negative | 980 | 3400 | + | + |
| 16 | At best response; off therapy | Negative | Negative | 761 | 1500 | + | + |
| 17 | Progressive disease; under therapy | 1:20 | Negative | 91 | 100 | − | − |
| 18 | Progressive disease; under therapy | Negative | Negative | 728 | 424 | + | + |
| 19 | Progressive disease; under therapy | 1:10 | Negative | 795 | 339 | + | + |
| 20 | Progressive disease; under therapy | Negative | Negative | 120 | 80 | − | − |
| 21 | Progressive disease; under therapy | 1:20 | Negative | 3200 | 812 | + | + |
| 22 | Progressive disease; under therapy | Negative | Negative | 291 | 594 | + | + |
| 23 | Progressive disease; under therapy | Negative | Negative | 500 | 732 | + | + |
| 24 | Progressive disease; under therapy | 1:10 | Negative | 500 | 191 | + | − |
| 25 | Progressive disease; under therapy | 1:20 | Negative | 860 | 950 | + | + |
| 26 | Active disease; under therapy | 1:20 | Negative | 195 | 162 | − | − |
| 27 | Progressive disease; under therapy | 1:5 | Negative | 222 | 976 | − | + |
| Percentage of patients with positive anti-MUC1 SP and MUC1 TRA specific antibodies levels | | | | | | 14/27 | 20/27 |

[1]Sera levels of MUC1 antigen and anti-MUC1 antibodies were measured by ELISA assay as described above. Positive sMUC1 level is set for titer of X > 1:5.
[2]Naïve sera for anti-MUC1 TRA antibodies epitope is X ≤ 274 µg/ml and for anti-MUC1 SP autoantibodies is X ≤ 210.2 µg/ml, based on the average plus standard deviation values determined in 15 naïve healthy individuals.

As demonstrated in Table 4, expression of sMUC1 in sera samples obtained from naïve healthy donors was low to undetectable, referred to as "negative" (at a titer level of less than 1:5). However, the level of sMUC1 was significantly higher (up to 8-fold, at a titer level of ≤1:40) in a large portion of patients. These results are consistent with the current knowledge of soluble MUC1 expression in naïve healthy donors and in cancer patients, having MUC1 positive tumors.

Example 9

Sera Expression Levels of MUC1 SP in Healthy Donors and Cancer Patients

The expression levels of soluble MUC1 SP in sera samples obtained from naïve healthy donors and from cancer patients were determined using the SPImAb-3A anti-SP polyclonal antibody, in an MBA assay, as described above. SPImAh-3A anti-SP polyclonal antibody is an IgG fraction of polyclonal hyper immune sera (obtained from rabbit), which is directed against the MUC1 SP-derived peptide, VXL100, which consists of the complete SP of MUC-1.

The results obtained for naïve healthy donors and for MM patients, which are at various disease stages are summarized in Tables 4 and 6. Expression of soluble MUC1 SP, as measured using the R23 antibody, was not observed neither in the sera of naïve healthy donors nor in the sera of MM patients. Namely, there is no correlation between disease stage and the level of soluble SP fragments of MUC1 or the level of the endogenously generated antibodies produced against cellular/surface SP.

Example 10

Sera Expression Levels of Endogenous Anti-MUC1 Antibodies in Healthy Donors and Cancer Patients The expression levels of endogenously generated antibodies to peptides derived from MUC1 were analyzed. Particularly, expression levels of endogenous antibodies which recognize VXL25 (a peptide derived from MUC1 TRA) as well as endogenous antibodies which recognize VXL100 and VXL3A (peptides derived from MUC1 SP), were evaluated in sera samples obtained from naïve healthy donors and cancer patients.

The expression levels of the endogenously generated antibodies described above were evaluated using an ELISA assay. Briefly, ELISA plates (F96 Maxisorp, Nunc, Roskild, Denmark) were activated by 0.1% of glutaraldehyde in carbonate buffer pH 9 for 1 h at RT and coated with 50 µl of MUC1-TRA-L peptide at 5 µg/ml in carbonate buffer and incubated overnight at 4° C. Plates were then blocked with 200 µl of PBS supplemented with 0.5% gelatin for 2 h at 25° C. Evaluated sera samples were then diluted 1:100 in PBS with 0.5% gelatin and incubated for 2 h at 25° C. Next, 50 µl/well of the appropriate secondary anti-IgG antibody HRP-conjugate (CHEMICON, Millipore, Billerica, Mass., USA) was added at a final dilution 1:10,000 in a blocking buffer and incubated for 1 h at 25° C. Plates were then developed as described above. For a positive standard, we used 6 double dilutions starting from 10 µg/ml of the anti-TRA mAb H23. In this assay, naïve sera for MUC1 are X <200 µg/ml, based on a mean value determined from 10 healthy individuals.

The monoclonal antibody (mAb) H23 was used as a positive control, by preparing six double dilutions (starting from 10 µg/ml) of this antibody. The monoclonal antibody H23 was raised against the human breast cancer cell line T47D, and recognizes the APDTRP epitope of the non-glycosylated form of MUC1 TRA (Keydar I, et al. *Proc Natl Acad Sci USA* 1989, 86:1362-1366). H23 is capable of recognizing soluble MUC1 TRA domain in sera or on cancer cells. It also recognizes the 25-mer peptide VXL25 (derived from MUC1 TRA, as described before).

The results obtained for naïve healthy donors and cancer patients with different cancers and at different stages of the disease are presented in Tables 4-6.

As demonstrated in Table 4, expression levels of 137.2±72.97 and 208.6±65.35 µg/ml were observed for anti-MUC1 SP endogenous antibody (which binds to VXL3A), and anti-MUC1 TRA antibodies, respectively, in naïve healthy donors. Surprisingly, the expression levels of antibodies to the MUC1 peptides, namely anti-VXL3A, and anti-VXL25 (TRA), were significantly elevated (3-7 folds) for the different cancer patients (Tables 5 and 6), while the expression level of antibodies to the non-TAA, Tuberculosis-derived SP VXL211 was very low (Table 5). These results confirm the existence of endogenously generated antibodies to MUC1 SP in cancer patients.

Importantly, a high concentration of anti-MUC1 SP autoantibodies was also present in patients with minimal disease (characterized as 'patients at best response off therapy'), four of which (namely, patients number 8, 10, 13 and 16) had undetectable sMUC1 levels, suggesting a potential role for these anti-MUC1 SP autoantibodies in detecting a disease at an early stage and possibly the disease onset.

The preferred immunogenicity of the MUC1 SP vs. the MUC1 TRA domain can be further demonstrated using the same group of patients, in which the concentration of the anti-SP auto antibodies was significantly higher (P<0.03, t-test) than that of the anti-MUC1 TRA levels. For these patients, any potential influence on sMUC1 levels by anti-MUC1 TRA autoantibodies was ruled out with a dedicated ELISA that analyzed the amount of sMUC1 in antigen-antibody complexes. This further supports the immunodominant properties of MUC1 SP regarding antibody production.

The percentage of patients having a "positive" anti-MUC1 SP or MUC1 TRA-specific titers was further analyzed. A positive response was defined for the average titer plus one standard deviation, as described below.

As a positive standard for anti-MUC1 TRA antibodies, dilutions starting with 10 µg/ml of the anti-MUC1 TRA mAb H23 [Keydar, I. et al. PNAS 86:1362-1366 (1989)] were used. These antibodies were raised against the human breast cancer cell line T47D and recognized the TRA epitope APDTRP on the non-glycosylated form of MUC1. As a positive standard for anti-MUC1 SP antibodies, dilutions beginning with 10 µg/ml of anti-MUC1-SP-M rabbit polyclonal antibodies were used. In this assay, serum levels for anti-MUC1 TRA autoantibodies in naïve donors were X≤274 µg/ml and for anti-MUC1 SP autoantibodies, X≤210.2 µg/ml, based on the average plus standard deviation value determined in 15 naïve healthy individuals.

The resulting analysis presented in Table 6 further supports the initial observation of an elevated production of anti-MUC1 SP autoantibodies. In particular, most patients, 20/27 (74%) had positive anti-MUC1 SP-specific autoantibodies, while only 14/27 (51.8%) had positive anti-MUC1 TRA-specific autoantibodies. These differences demonstrated a positive trend for the selectivity of MUC1's SP vs. TRA domain in multiple myeloma patients.

Since, as mentioned above, expression of MUC1 SP was not observed in the sera of naïve healthy donors or MM patients, the target antigen (or epitope) for the endogenously generated anti-MUC1 SP could possibility be expressed on the cell surface of cancer cells. Expression of MUC1 SP on cell surface may be either as an independent molecule and/or in association with MHC molecules.

The low expression levels of antibodies obtained for the non-TAA SP VXL211 (derived from the MTb protein, Rv0476/MTO4941) in naïve donors and in cancer patients, is consistent with the expression of MUC1 SP as a cancer-specific marker (or target) rather than an SP non-specific response.

Interestingly, the most significant results, having the lowest standard deviations, were detected in the case of the MUC1 SP peptide VXL3A, in all types of cancers tested. Consistently, the difference in the expression levels of endogenously generated anti-VXL3A antibodies between naïve healthy donors and cancer patients of all cancer types has the highest statistical difference, as verified by a t-test shown in Table 7 (0.0007-0.01). A similar analysis, performed for anti-VXL100 endogenous antibodies showed that while the difference in the expression levels obtained for naïve healthy donors and for cancer patients was less prominent than in the case of the anti-VXL3A endogenous antibodies, the difference was still significant, mainly in sera samples of patients with solid tumors (Table 7).

TABLE 7

| T-Test (two tails) | Anti VXL25 Ab | AntiVX100 Ab | Anti VXL3A Ab |
|---|---|---|---|
| S | 0.05426591 | 0.02541475 | 0.0101179 |
| B | 0.04110985 | 0.00850219 | 0.0007251 |
| H | 0.05924422 | 0.04359874 | 0.0030535 |

Significantly, these results suggest that the VXL3A sequence, which consists of the 10-21 C-terminal 12 amino acids of the 21 amino acids peptide VXL100, is of greater specificity for the endogenously generated antibodies. The lower variability obtained for the endogenously generated antibodies to the VXL3A peptide is consistent with these findings.

Inferior results were obtained with the same sera samples for the MUC TRA peptide. According to the statistical t-test conducted in this case, the difference in the concentration of endogenously generated anti-VXL25 antibodies is of (marginal) significance only for patients with solid tumors (Table 7, 0.008). These results are consistent with previous publications, which showed a high variation in the levels of endogenously generated antibodies to MUC1 TRA sequences, such as VXL25, in cancer patients.

Example 11

Correlation Between Sera Expression Levels of Endogenous Anti-MUC1 SP Antibodies and sMUC1

Figure 7D:
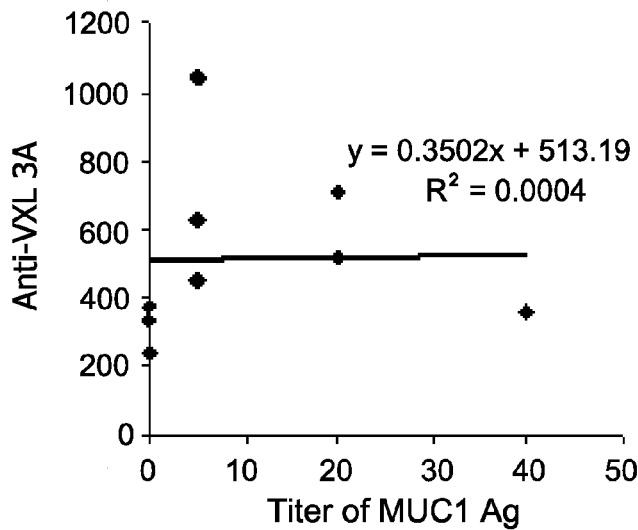
Figure 7E:
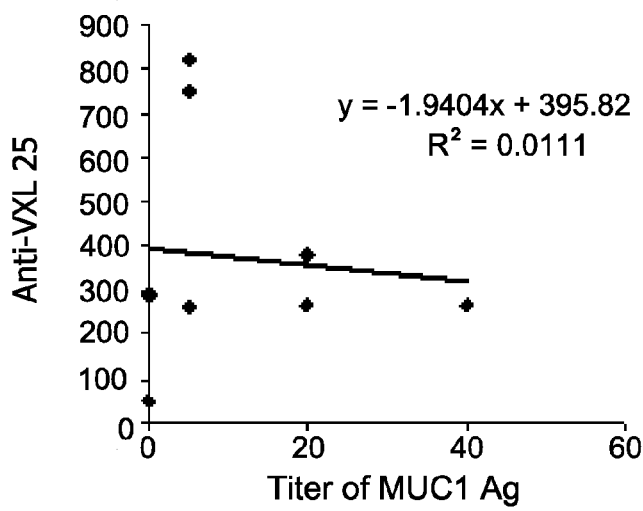
Figure 7F:
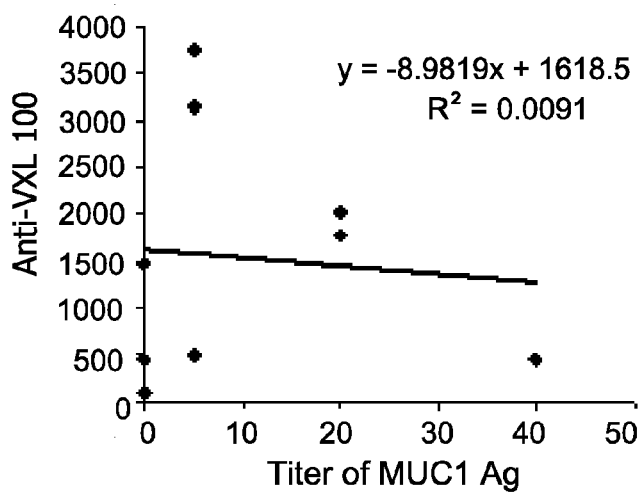

The levels of sMUC1 (MUC1 Ag) were compared with the levels of endogenously generated antibodies against VXL3A, VXL100 and VXL25, as described above, for a group of 25 cancer patients having non-solid tumors (MM, FIG. 7, A-C) and for 10 cancer patients having solid tumors, in particular Colon, Rectal, Lung, and Prostate (FIG. 7, D-F). As demonstrated in FIG. 7A a positive correlation was observed for the sera levels of sMUC1 and the sera level of endogenously-generated anti-VXL3A antibodies, for MM patients ($R^2$=0.475 for all 25 patients assayed). Most interestingly, a higher correlation ($R^2$=0.7606) was demonstrated for patients having an advanced stage of the cancer disease (16 out of the 25 patients).

Lower correlations, of $R^2=0.165$ and $R^2=0.081$, were found for endogenously-generated anti-VXL25 antibodies (FIG. 7B) and anti-VXL100 antibodies (FIG. 7C), respectively, within the same assay and patients.

As demonstrated in FIG. 7 D-F, a similar analysis performed with patients with solid tumors manifested no correlation between the levels of sMUC1 and the levels of endogenously generated antibodies against any of the peptides, namely VXL25, VXL100, VXL3A ($R^2=0.011$, 0.0091 and 0.004 respectively).

These results can possibly be related to the large diversity in the levels of sMUC1 in patients with solid tumor vs. patients with non-solid tumor. Particularly, these results may possibly be attributed to the fact that most of the patients analyzed in this group had surgery for tumor removal, which may potentially result in the reduction of the level of sMUC1.

Example 12

Correlation Between Sera Levels of the Different Anti-MUC1 Antibodies

The half-life of endogenously generated antibodies in the sera of patients is relatively prolonged and is not immediately influenced by the levels of the antigen. The concentrations of the various anti-MUC1 peptide antibodies were inter-correlated, as described above. The results obtained for patients with solid tumors (FIG. 8, C and D) showed a positive correlation between the titer levels of anti-VXL3A and anti-VXL25 antibodies (D) ($R^2=0.4511$). However, no correlation ($R^2=0.0733$) was found between the titer levels of anti-VXL25 and anti-VX100 antibodies (C).

Similar analysis conducted for MM patients (FIG. 8, A and B) manifested an inverse correlation pattern. While a positive correlation ($R^2=0.5665$) was observed for the titer levels of anti-VXL25 and anti-VX100 antibodies (FIG. 8, A), no correlation was found between the titer levels of anti-VXL3A and anti-VXL25 antibodies (FIG. 8, B) ($R^2=0.0992$). These results may potentially be used for developing a tool for early detection of MUC1 positive tumors, before disease onset, or for developing a tool for monitoring disease progression.

Example 13

Sera Expression Levels of Endogenous Antibodies to MUC1 SP in BRCA Carriers

A BRCA mutation is a mutation in either of the genes BRCA1 or BRCA2. Harmful mutations in these genes produce hereditary breast-ovarian cancers in affected families. Hundreds of different types of mutations in these genes have been identified. Women with harmful mutations in either BRCA1 or BRCA2 have risk of breast cancer that is about five times the normal risk, and a risk of ovarian cancer that is about ten to thirty times the normal risk.

However, at present, the available diagnostic tests do not enable the detection of all of these mutations. In addition, early detection of breast and ovarian cancers is limited, since appropriate markers that signal mutations in the BRCA genes are currently not available.

The expression levels of endogenously generated antibodies which recognize VXL25 (a peptide derived from MUC1 TRA) as well as endogenous antibodies which recognize VXL100 and VXL3A (peptides derived from MUC1 SP), were evaluated in sera samples obtained from BRCA1/2(−) and BRCA1(+) and BRCA2(+) carriers.

Figure 9A:
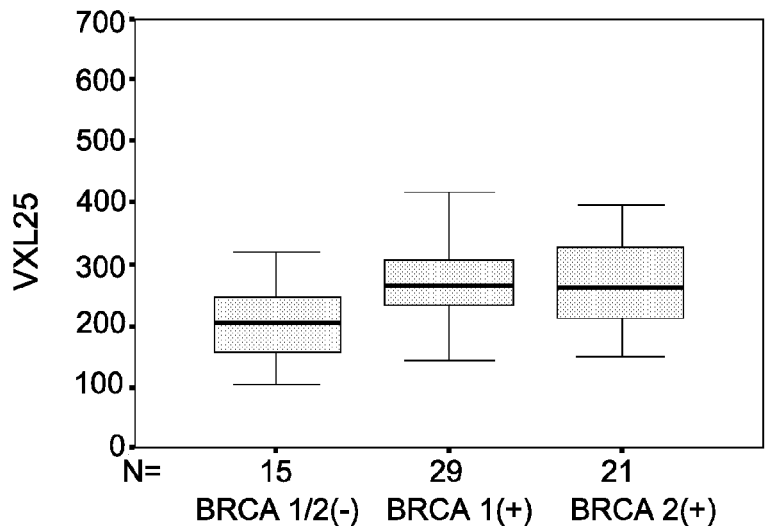
FIG. 9A-9C is a graphical representation of the expression levels of endogenously generated antibodies which recognize VXL25 (FIG. 9A), VXL100 (FIG. 309B) and VXL3A (FIG. 9C) in BRCA 1/2 (−), BRCA1 (+) or BRCA2 (+) carriers.
Figure 9B:
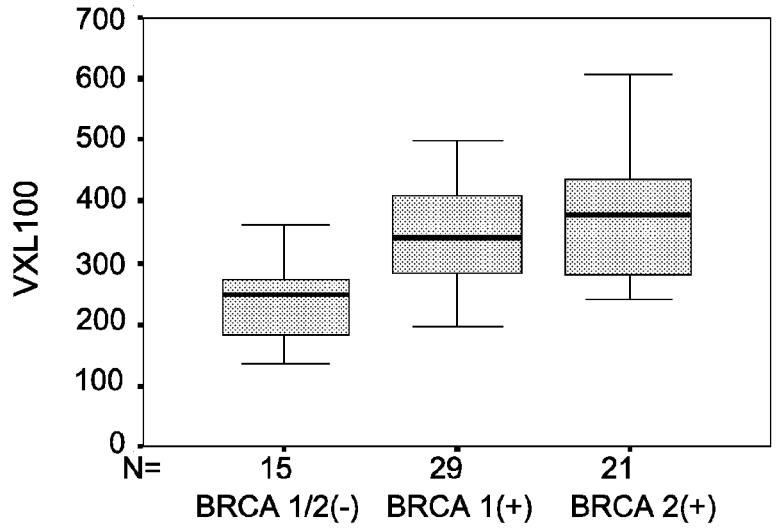
Figure 9C:
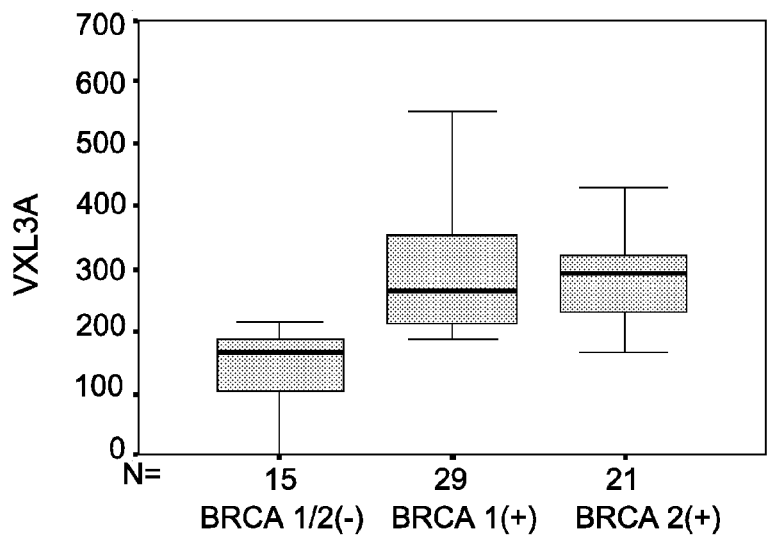

As demonstrated in FIG. 9B, the expression levels of endogenously generated antibodies which recognize VXL100 were significantly higher in BRCA1 (+) and BRCA2 (+) carriers (n=29, 21, respectively) than in BRCA1/2(−) carriers (n=15), with the t-test values p=0.001 and p<0.001, respectively. Similarly, as demonstrated in FIG. 9C, the expression levels of endogenously generated antibodies which recognize VXL3A were significantly higher in BRCA1 (+) and BRCA2 (+) carriers than in BRCA1/2(−) carriers (p<0.001). No significant difference was found between the levels of endogenously generated antibodies which recognize VXL25 in BRCA1 (+), BRCA2 (+) or BRCA1/2(−) carriers (FIG. 9A). The mean age for all the subjects tested was 38 (20-73 years).

The correlation between the levels of endogenous antibodies directed to MUC1 SP and the presence of the BRCA1 and/or BRCA2 gene mutation show that the autoantibody levels of these antibodies may be used for detection of cancers associated with BRCA mutations, e.g. breast and ovarian cancers.

Example 14

Levels of Endogenous Antibodies Directed to Non-MUC1 TAA SP in Sera of Cancer Patients The endogenously generated antibody titers to SP domains of various TAAs were evaluated as described above, in particular for ARMET (VXL101), Uroplakin II (VXL104), PAP (VXL106) and Mammaglobin-1 (VXL108). The analysis was performed for MM patients (Table 8 A) and patients with solid tumors (Table 8 B). Results demonstrated that endogenously generated antibodies exist also for these TAA SPs, and these antibodies may thus be used for diagnosis as discussed above.

TABLE 8

Sera levels of antibodies to non-MUC1 TAA SP in cancer patients

| Patient | Indication | Anti VXL100 (titer) | Anti VXL101 (titer) | Anti VXL104 (titer) | Anti VXL106 (titer) | Anti VXL108 (titer) |
|---|---|---|---|---|---|---|
| | | | A | | | |
| H#2 | MM | 1:3200 | 1:200 | 1:100 | 1:100 | 1:100 |
| H#3 | MM | 1:3200 | 1:200 | 1:100 | 1:100 | 1:100 |
| H#5 | MM | 1:12800 | 1:200 | 1:100 | 1:100 | 1:100 |
| H#8 | MM | 1:1600 | 1:200 | 1:100 | 1:100 | 1:100 |

TABLE 8-continued

Sera levels of antibodies to non-MUC1 TAA SP in cancer patients

| Patient | Indication | Anti VXL100 (titer) | Anti VXL101 (titer) | Anti VXL104 (titer) | Anti VXL106 (titer) | Anti VXL108 (titer) |
|---------|------------|---------------------|---------------------|---------------------|---------------------|---------------------|
| | | B | | | | |
| B#2 | Colon | 1:3200 | 1:200 | 1:200 | 1:200 | 1:100 |
| B#3 | Colorectal | 1:6400 | 1:200 | 1:200 | 1:200 | 1:100 |
| B#4 | Colorectal | 1:6400 | 1:200 | 1:200 | 1:200 | 1:100 |
| B#7 | Colon | 1:800 | 1:200 | 1:200 | 1:400 | 1:100 |
| B#9 | Chorionic | 1:200 | 1:800 | 1:400 | 1:800 | 1:400 |

Example 16

Levels of Antibodies to SP in Sera of Tuberculosis Patients

The expression levels of endogenously generated antibodies to five immunogenic SP domains from key antigens in MTb were analyzed, particularly, Antigen 85B (VXL201), Lipoprotein lpqH (VXL203), ATP dependent helicase putative (VXL 208), Uncharacterized protein Rv0476/MTO4941 precursor (VXL 211) and Uncharacterized protein Rv1334/MT1376 precursor (VXL 212).

SP selection for these assays was based on the immunodominant properties of these MTb peptides, particularly, the strong proliferation ability of the SP domains on a large pool of naïve healthy donors and MTb patients, and further, the high IL2 secretion by stimulated T cells, obtained from naïve donors, that correlated with theirs helper function to support antibody production (Kovjazin, R. et al., Mol Immunol 2011, 48:1009-1018).

Table 9 presents the results obtained for seven naïve healthy donors and for seven patients having active tuberculosis. The results are present for individual samples and also as an average±standard deviation for the naïve healthy donors as well as for the patients. In naïve healthy donors (Table 9, B) expression levels of 285±146, 257.6±97, 214±134, 185±146 and 185±146 were obtained, for anti-VXL201, VXL203, VXL208, VXL211 and VXL211 endogenous antibodies, respectively. The concentration of endogenously generated antibodies to all five MTb SP Vaccine candidates was found to be elevated (3.2-39.5 folds) in tuberculosis (MTb) patients (Table 9, A).

TABLE 9

Sera levels of antibodies to SP in tuberculosis patients and Naïve donors

| | VXL201 | VXL203 | VXL208 | VXL211 | VXL212 |
|---|--------|--------|--------|--------|--------|
| | A | | | | |
| P#1 | 1600 | 3200 | 12800 | 1600 | 800 |
| P#3 | 800 | 3200 | 12800 | 800 | 800 |
| P#13 | 1600 | 3200 | 12800 | 1600 | 800 |
| P#14 | 400 | 800 | 1600 | 400 | 400 |
| P#17 | 400 | 1600 | 3200 | 800 | 400 |
| P#18 | 800 | 1600 | 12800 | 1600 | 800 |
| P#19 | 800 | 1600 | 3200 | 800 | 400 |
| Average | 914.29 | 2171.43 | 8457.14 | 1085.71 | 628.57 |
| STDVE | 501.43 | 1002.85 | 5442.69 | 501.43 | 213.81 |
| | B | | | | |
| ND#1 | 100 | 200 | 100 | 100 | 100 |
| ND#2 | 200 | 200 | 200 | 100 | 100 |

TABLE 9-continued

Sera levels of antibodies to SP in tuberculosis patients and Naïve donors

| | VXL201 | VXL203 | VXL208 | VXL211 | VXL212 |
|---|--------|--------|--------|--------|--------|
| ND#3 | 100 | 200 | 200 | 100 | 100 |
| ND#4 | 400 | 200 | 100 | 100 | 100 |
| ND#5 | 400 | 200 | 100 | 100 | 100 |
| ND#6 | 400 | 400 | 400 | 400 | 400 |
| ND#7 | 400 | 400 | 400 | 400 | 400 |
| Average | 285.71 | 257.14 | 214.29 | 185.71 | 185.71 |
| STDVE | 146.39 | 97.59 | 134.52 | 146.39 | 146.39 |
| Ratio P/N | 3.20 | 8.44 | 39.47 | 5.85 | 3.38 |

These results confirm the existence of endogenously generated antibodies to the five SP domains (particularly directed to the peptides VXL208 and VXL203) in tuberculosis patients.

Since in the case of VXL100 and VXL3A, low expression levels of SP fragments in the sera of naïve healthy donors were observed, it is plausible that the target antigen/epitopes for the endogenously generated SP may be expressed on the cell surface of bacteria and/or on MTb infected cells. Thus, SP expression may be either observed as an independent molecule and/or in association with MHC molecules.

Example 17

Induction of Humoral Response to SP of Various MTb Proteins in Mice

In a set of in vivo experiments, the immunogenicity and synergistic properties of a number of combinations of the five MTb SP Vaccine candidates (VC) referred to above in Example 16 (i.e. VXL201, VXL203, VXL208, VXL 211 and VXL212) were evaluated. Thus, 7 weeks old BALB/c mice were vaccinated two or three times at weekly intervals with a total of 100 μg per mouse of the following mixtures:

Mixture 1: VXL201, VXL203, VXL208, VXL211 and VXL212; Mixture 2: VXL201, VXL203, VXL211 and VXL212; Mixture 3: VXL201 and VXL 203; and Mixture 4: VXL211 and VXL 212. The mixtures were dissolve in DMSO (Sigma Aldrich Israel/PBS and administered to mice without the addition of a carrier or an adjuvant. Even in the absence of an adjuvant, a hyper immune sera was unpredictably generated to few of the SP mixtures, mainly to Mixture 3 (VXL201 and VXL203), as to demonstrated in Table 10. In addition, these surprising results were obtained after merely two vaccinations.

TABLE 10

Induction of humoral response to MTb SP in BALB/c mice

A

| Evaluated Peptide | Mix1*3 | Mix1*2 | Mix2*3 | Mix2*2 | Mix3*3 | Mix3*2 | Mix4*3 | Mix4*2 | PBS |
|---|---|---|---|---|---|---|---|---|---|
| | | | | Serum titer | | | | | |
| VXL201 | 1:800 | 1:400 | 1:1600 | 1:1600 | 1:3200 | 1:3200 | 1:100 | 1:100 | 1:100 |
| VXL203 | 1:800 | 1:400 | 1:1600 | 1:1600 | 1:3200 | 1:3200 | 1:100 | 1:100 | 1:100 |
| VXL208 | 1:400 | 1:400 | 1:800 | 1:400 | 1:800 | 1:400 | 1:100 | 1:100 | 1:100 |
| VXL211 | 1:400 | 1:400 | 1:400 | 1:400 | 1:100 | 1:100 | 1:100 | 1:100 | 1:100 |
| VXL212 | 1:400 | 1:400 | 1:400 | 1:400 | 1:100 | 1:100 | 1:100 | 1:100 | 1:100 |

B

| Mouse | VXL201 | VXL203 | VXL211 |
|---|---|---|---|
| 1 | 1:24000 | 1:1600 | 1:200 |
| 2 | 1:24000 | 1:3200 | 1:200 |
| 3 | 1:1600 | 1:3200 | 1:200 |
| 4 | 1:24000 | 1:800 | 1:200 |

This humoral response (Table 10) did not interfere with a robust T-cell response to these mixtures, as evaluated by proliferation and cytotoxicity. The results shown in Table 10A demonstrate a significant elevation in the anti-VXL201 and in the anti-VXL203 titers, following 2 or 3 vaccinations with Mixture 3. Based on these results, the vaccination regimen was repeated (3 times) at weekly intervals in four BALB/c mice, using only Mixture 3. The results obtained in this experiment (Table 10B) showed a highly significant and specific titer, of up to 1:24,000 in three out of the four mice tested, mainly to Vaccine candidates (VC) VXL201. The titer to VXL203, the second peptide in this Mixture, was specific, but significantly lower than that obtained for VXL201. On the other hand, the response to VXL211 VC evaluated in this experiment as a control SP did not induce any antibody titer.

Example 18

Antibodies Recognize VXL201 and VXL203 on the Cell Surface of MTb Cells

As shown above, vaccination of mice with Mixture 3 was able to generate specific antibodies that recognize VXL201 and to some extent also VXL203. The following example demonstrates that these epitopes are specifically expressed on MTb bacterial cells and are recognized by the antibodies on the cell surface.

Hyperimmune sera with high titer were used for immunofluorescence staining of MTb bacteria (FIG. 10 D), as well as for staining of a related mycobacterium strain, the *M. Kansasii* (FIG. 10 E). The existence of bacteria in the preparations was confirmed using 4'-6-Diamidino-2-phenylindole (DAPI) DNA staining (FIG. 10, A-C). The results clearly showed specific binding by the hyper immune sera only in the case of the MTb bacteria (upper Right), while no staining of the *Mycobacterium Kansasi* was observed (middle right panel). In addition, no binding was observed for MTb, when sera from normal mice were used (FIG. 10 F).

---

The invention claimed is:

1. A method for detecting a presence of autoantibodies directed against MUC1 SP in a biological sample, said method comprising:
    a. obtaining a biological sample from a subject; and
    b. measuring the level of autoantibodies directed against said MUC1 SP, or any fragment thereof, by contacting said biological sample with MUC1 SP, or any fragment thereof.

2. The method according to claim 1, wherein said MUC1 SP, or any fragment thereof, is a peptide selected from a group consisting of the peptides denoted by SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, and SEQ ID NO. 10.

3. The method according to claim 2, wherein said MUC1 SP, or any fragment thereof, is a peptide denoted by SEQ ID NO. 3.

* * * * *

SEQUENCE LISTING

<160> NUMBER OF SEQ ID NOS: 20

<210> SEQ ID NO 1
<211> LENGTH: 25
<212> TYPE: PRT
<213> ORGANISM: Homo sapiens

<400> SEQUENCE: 1

Ser Thr Ala Pro Pro Ala His Gly Val Thr Ser Ala Pro Asp Thr Arg
1               5                   10                  15

Pro Ala Pro Gly Ser Thr Ala Pro Pro
            20                  25

<210> SEQ ID NO 2
<211> LENGTH: 21
<212> TYPE: PRT
<213> ORGANISM: Homo sapiens

<400> SEQUENCE: 2

Met Thr Pro Gly Thr Gln Ser Pro Phe Phe Leu Leu Leu Leu Leu Thr
1               5                   10                  15

Val Leu Thr Val Val
            20

<210> SEQ ID NO 3
<211> LENGTH: 17
<212> TYPE: PRT
<213> ORGANISM: Homo sapiens

<400> SEQUENCE: 3

Lys Lys Phe Leu Leu Leu Leu Thr Val Leu Thr Val Val Lys Lys
1               5                   10                  15

Lys

<210> SEQ ID NO 4
<211> LENGTH: 9
<212> TYPE: PRT
<213> ORGANISM: Homo sapiens

<400> SEQUENCE: 4

Leu Leu Leu Thr Val Leu Thr Val Val
1               5

<210> SEQ ID NO 5
<211> LENGTH: 9
<212> TYPE: PRT
<213> ORGANISM: Homo sapiens

<400> SEQUENCE: 5

Leu Leu Leu Leu Thr Val Leu Thr Val
1               5

<210> SEQ ID NO 6
<211> LENGTH: 9
<212> TYPE: PRT
<213> ORGANISM: Homo sapiens

<400> SEQUENCE: 6

Phe Leu Leu Leu Leu Leu Thr Val Leu
1               5

<210> SEQ ID NO 7
<211> LENGTH: 9
<212> TYPE: PRT
<213> ORGANISM: Homo sapiens

<400> SEQUENCE: 7

Thr Gln Ser Pro Phe Phe Leu Leu Leu
1               5

<210> SEQ ID NO 8
<211> LENGTH: 9
<212> TYPE: PRT
<213> ORGANISM: Homo sapiens

<400> SEQUENCE: 8

Ser Pro Phe Phe Leu Leu Leu Leu Leu
1               5

```
<210> SEQ ID NO 9
<211> LENGTH: 9
<212> TYPE: PRT
<213> ORGANISM: Homo sapiens

<400> SEQUENCE: 9

Phe Phe Leu Leu Leu Leu Leu Thr Val
1               5

<210> SEQ ID NO 10
<211> LENGTH: 9
<212> TYPE: PRT
<213> ORGANISM: Homo sapiens

<400> SEQUENCE: 10

Met Thr Pro Gly Thr Gln Ser Pro Phe
1               5

<210> SEQ ID NO 11
<211> LENGTH: 21
<212> TYPE: PRT
<213> ORGANISM: Homo sapiens

<400> SEQUENCE: 11

Met Trp Ala Thr Gln Gly Leu Ala Val Ala Leu Ala Leu Ser Val Leu
1               5                   10                  15

Pro Gly Ser Arg Ala
            20

<210> SEQ ID NO 12
<211> LENGTH: 17
<212> TYPE: PRT
<213> ORGANISM: Homo sapiens

<400> SEQUENCE: 12

Met Ala Ala Arg Ala Val Phe Leu Ala Leu Ser Ala Gln Leu Leu Gln
1               5                   10                  15

Ala

<210> SEQ ID NO 13
<211> LENGTH: 25
<212> TYPE: PRT
<213> ORGANISM: Homo sapiens

<400> SEQUENCE: 13

Met Ala Pro Leu Leu Pro Ile Arg Thr Leu Pro Leu Ile Leu Ile Leu
1               5                   10                  15

Leu Ala Leu Leu Ser Pro Gly Ala Ala
            20                  25

<210> SEQ ID NO 14
<211> LENGTH: 27
<212> TYPE: PRT
<213> ORGANISM: Homo sapiens

<400> SEQUENCE: 14

Met Phe Asp Lys Thr Arg Leu Pro Tyr Val Ala Leu Asp Val Leu Cys
1               5                   10                  15

Val Leu Leu Ala Gly Leu Pro Phe Ala Ile Leu
            20                  25
```

```
<210> SEQ ID NO 15
<211> LENGTH: 18
<212> TYPE: PRT
<213> ORGANISM: Homo sapiens

<400> SEQUENCE: 15

Met Lys Leu Leu Met Val Leu Met Leu Ala Ala Leu Ser Gln His Cys
1               5                   10                  15

Tyr Ala

<210> SEQ ID NO 16
<211> LENGTH: 40
<212> TYPE: PRT
<213> ORGANISM: Mycobacterium tuberculosis

<400> SEQUENCE: 16

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
                20                  25                  30

Gly Gly Ala Ala Thr Ala Gly Ala
            35                  40

<210> SEQ ID NO 17
<211> LENGTH: 24
<212> TYPE: PRT
<213> ORGANISM: Mycobacterium tuberculosis

<400> SEQUENCE: 17

Met Lys Arg Gly Leu Thr Val Ala Val Ala Gly Ala Ala Ile Leu Val
1               5                   10                  15

Ala Gly Leu Ser Gly Cys Ser Ser
            20

<210> SEQ ID NO 18
<211> LENGTH: 32
<212> TYPE: PRT
<213> ORGANISM: Mycobacterium tuberculosis

<400> SEQUENCE: 18

Met Arg Phe Ala Gln Pro Ser Ala Leu Ser Arg Phe Ser Ala Leu Thr
1               5                   10                  15

Arg Asp Trp Phe Thr Ser Thr Phe Ala Ala Pro Thr Ala Ala Gln Ala
                20                  25                  30

<210> SEQ ID NO 19
<211> LENGTH: 19
<212> TYPE: PRT
<213> ORGANISM: Mycobacterium tuberculosis

<400> SEQUENCE: 19

Met Leu Val Leu Leu Val Ala Val Leu Val Thr Ala Val Tyr Ala Phe
1               5                   10                  15

Val His Ala

<210> SEQ ID NO 20
<211> LENGTH: 25
<212> TYPE: PRT
<213> ORGANISM: Mycobacterium tuberculosis
```

-continued

```
<400> SEQUENCE: 20

Met Leu Leu Arg Lys Gly Thr Val Tyr Val Leu Val Ile Arg Ala Asp
1               5                   10                  15

Leu Val Asn Ala Met Val Ala His Ala
            20                  25
```